United States Patent
Junger et al.

(10) Patent No.: US 11,147,954 B2
(45) Date of Patent: Oct. 19, 2021

(54) MICROPROJECTION ARRAY APPLICATOR AND METHOD

(71) Applicant: Vaxxas Pty Limited, Sydney (AU)

(72) Inventors: Michael Carl Junger, Brookfield (AU); Pierre Armand Vincent Lemaire, Dutton Park (AU)

(73) Assignee: VAXXAS PTY LIMITED, Sydney (AU)

( * ) Notice: Subject to any disclaimer, the term of this patent is extended or adjusted under 35 U.S.C. 154(b) by 348 days.

(21) Appl. No.: 15/548,065

(22) PCT Filed: Feb. 2, 2016

(86) PCT No.: PCT/AU2016/050056
§ 371 (c)(1),
(2) Date: Aug. 1, 2017

(87) PCT Pub. No.: WO2016/123665
PCT Pub. Date: Aug. 11, 2016

(65) Prior Publication Data
US 2018/0015271 A1    Jan. 18, 2018

Related U.S. Application Data

(60) Provisional application No. 62/110,682, filed on Feb. 2, 2015.

(51) Int. Cl.
*A61M 37/00*    (2006.01)

(52) U.S. Cl.
CPC ... *A61M 37/0015* (2013.01); *A61M 2037/003* (2013.01); *A61M 2037/0023* (2013.01);
(Continued)

(58) Field of Classification Search
CPC ...... A61M 37/0015; A61M 2037/0023; A61M 2037/003; A61M 2037/0046; A61M 2037/0061; A61M 5/148
See application file for complete search history.

(56) References Cited

U.S. PATENT DOCUMENTS

| | | |
|---|---|---|
| 2,213,830 A | 9/1940 | Anastasi |
| 2,881,500 A | 4/1959 | Furness |

(Continued)

FOREIGN PATENT DOCUMENTS

| | | |
|---|---|---|
| CN | 1149018 A | 5/1997 |
| CN | 101214395 A | 7/2008 |

(Continued)

OTHER PUBLICATIONS

Aichele et al., "Antiviral Cytotoxic T Cell Response Induced by In Vivo Priming With a Free Synthetic Peptide," *J. Exp. Med.* 171:1815-1820, 1990.
(Continued)

*Primary Examiner* — Tiffany Legette
(74) *Attorney, Agent, or Firm* — Seed IP Law Group LLP

(57) ABSTRACT

The present invention relates to applicators for administering microprojection arrays to skin and methods of administering microprojection arrays. One embodiment of the present invention is a device for applying a microprojection array to a skin surface comprising: a) a housing having an upper and lower portion and having an internal face and an external face wherein the external face a flexible section that when collapsed actuates the device; b) a patch guide having a proximal and distal end wherein the proximal end interfaces with the internal face of the housing such that when the flexible section of the external face of the housing is collapsed the patch guide is forced downward; c) a cantilevered ring having an opening through which the patch guide passes and wherein the cantilevered ring is activated by the patch guide; d) a microprojection array that is contacted by the cantilevered ring when the ring is activated; e) a skin contact membrane; and f) a skin contact applicator base that attaches to the housing. A further embodiment of the present invention also includes two or more cantilevered rings
(Continued)

having a first and a last ring, wherein the cantilevered rings are stacked such that when the device is actuated the first ring is fired such that each successive ring is contacted by the preceding ring.

23 Claims, 13 Drawing Sheets

(52) U.S. Cl.
CPC ............... *A61M 2037/0046* (2013.01); *A61M 2037/0061* (2013.01)

(56) References Cited

U.S. PATENT DOCUMENTS

| | | | |
|---|---|---|---|
| 4,702,799 A | 10/1987 | Tuot | |
| 5,017,007 A | 5/1991 | Milne et al. | |
| 5,201,992 A | 4/1993 | Marcus et al. | |
| 5,353,792 A | 10/1994 | Lubbers et al. | |
| 5,449,064 A | 9/1995 | Hogan et al. | |
| 5,457,041 A | 10/1995 | Ginaven et al. | |
| 5,461,482 A | 10/1995 | Wilson et al. | |
| 5,499,474 A | 3/1996 | Knooihuizen | |
| 5,527,288 A | 6/1996 | Gross et al. | |
| 5,611,806 A | 3/1997 | Jang | |
| 5,657,138 A | 8/1997 | Lewis et al. | |
| 5,859,937 A | 1/1999 | Nomura | |
| 5,922,356 A | 7/1999 | Koseki et al. | |
| 5,928,207 A | 7/1999 | Pisano et al. | |
| 5,943,075 A | 8/1999 | Lee et al. | |
| 6,052,652 A | 4/2000 | Lee | |
| 6,233,797 B1 | 5/2001 | Neely et al. | |
| 6,287,556 B1 | 9/2001 | Portnoy et al. | |
| 6,299,621 B1 | 10/2001 | Fogarty et al. | |
| 6,334,856 B1 | 1/2002 | Allen et al. | |
| 6,352,697 B1 | 3/2002 | Cox et al. | |
| 6,454,755 B1 | 9/2002 | Godshall | |
| 6,463,312 B1 | 10/2002 | Bergveld et al. | |
| 6,478,738 B1 | 11/2002 | Hirabayashi et al. | |
| 6,503,231 B1 | 1/2003 | Prausnitz et al. | |
| 6,537,242 B1 | 3/2003 | Palmer | |
| 6,537,264 B1 | 3/2003 | Cormier et al. | |
| 6,551,849 B1 | 4/2003 | Kenney | |
| 6,557,849 B2 | 5/2003 | Wyss | |
| 6,558,361 B1 | 5/2003 | Yeshurun | |
| 6,565,532 B1 | 5/2003 | Yuzhakov et al. | |
| 6,589,202 B1 | 7/2003 | Powell | |
| 6,591,124 B2 | 7/2003 | Sherman et al. | |
| 6,610,382 B1 | 8/2003 | Kobe et al. | |
| 6,743,211 B1 | 6/2004 | Prausnitz et al. | |
| 6,749,575 B2 | 6/2004 | Matriano et al. | |
| 6,855,372 B2 | 2/2005 | Trautman et al. | |
| 6,881,203 B2 | 4/2005 | Delmore et al. | |
| 6,908,453 B2 | 6/2005 | Fleming et al. | |
| 6,923,764 B2 | 8/2005 | Aceti et al. | |
| 6,931,277 B1 | 8/2005 | Yuzhakov et al. | |
| 6,945,952 B2 | 9/2005 | Kwon | |
| 7,022,071 B2 | 4/2006 | Schaupp et al. | |
| 7,045,069 B2 | 5/2006 | Ozeryansky | |
| 7,097,631 B2 | 8/2006 | Trautman et al. | |
| 7,169,600 B2 | 1/2007 | Hoss et al. | |
| 7,211,062 B2 | 5/2007 | Kwon | |
| 7,250,037 B2 | 7/2007 | Shermer et al. | |
| 7,316,665 B2 | 1/2008 | Laurent et al. | |
| 7,753,888 B2 | 7/2010 | Mukerjee et al. | |
| 8,052,633 B2 | 11/2011 | Kendall | |
| 8,062,573 B2 | 11/2011 | Kwon | |
| 8,267,889 B2 | 9/2012 | Cantor et al. | |
| 8,414,548 B2 | 4/2013 | Yuzhakov | |
| 8,540,672 B2 | 9/2013 | McAllister | |
| 8,734,697 B2 | 5/2014 | Chen et al. | |
| 8,883,015 B2 | 11/2014 | Kendall et al. | |
| 9,283,365 B2 | 3/2016 | Kendall et al. | |
| 2002/0008530 A1 | 1/2002 | Kim et al. | |
| 2002/0016562 A1 | 2/2002 | Cormier et al. | |
| 2002/0032415 A1 | 3/2002 | Trautman et al. | |
| 2002/0128599 A1 | 9/2002 | Cormier et al. | |
| 2002/0133129 A1 | 9/2002 | Arias et al. | |
| 2002/0177839 A1 | 11/2002 | Cormier et al. | |
| 2003/0036710 A1 | 2/2003 | Matriano et al. | |
| 2003/0199810 A1 | 10/2003 | Trautman et al. | |
| 2003/0199811 A1 | 10/2003 | Sage, Jr. et al. | |
| 2003/0220656 A1 | 11/2003 | Gartstein et al. | |
| 2004/0002121 A1 | 1/2004 | Regan et al. | |
| 2004/0004649 A1 | 1/2004 | Bibl et al. | |
| 2004/0008241 A1 | 1/2004 | Junhua | |
| 2004/0039397 A1 | 2/2004 | Weber et al. | |
| 2004/0087992 A1 | 5/2004 | Gartstein et al. | |
| 2004/0161470 A1 | 8/2004 | Andrianov et al. | |
| 2005/0042866 A1 | 2/2005 | Klapproth et al. | |
| 2005/0089553 A1 | 4/2005 | Cormier et al. | |
| 2005/0089554 A1 | 4/2005 | Cormier et al. | |
| 2005/0126710 A1 | 6/2005 | Laermer et al. | |
| 2005/0137531 A1 | 6/2005 | Prausnitz et al. | |
| 2005/0143713 A1 | 6/2005 | Delmore et al. | |
| 2005/0197308 A1 | 9/2005 | Dalton et al. | |
| 2005/0261632 A1 | 11/2005 | Xu | |
| 2006/0012780 A1 | 1/2006 | Nishiyama et al. | |
| 2006/0015061 A1 | 1/2006 | Kuo et al. | |
| 2006/0055724 A1 | 3/2006 | Krawczyk et al. | |
| 2006/0074376 A1 | 4/2006 | Kwon | |
| 2006/0195125 A1 | 8/2006 | Sakakine et al. | |
| 2006/0202385 A1 | 9/2006 | Xu et al. | |
| 2006/0264782 A1 | 11/2006 | Holmes et al. | |
| 2007/0027474 A1 | 2/2007 | Lasner | |
| 2007/0060867 A1 | 3/2007 | Xu | |
| 2007/0078376 A1 | 4/2007 | Smith | |
| 2007/0224252 A1 | 9/2007 | Trautman et al. | |
| 2007/0264749 A1 | 11/2007 | Birkmeyer | |
| 2007/0270738 A1 | 11/2007 | Wu et al. | |
| 2007/0293815 A1 | 12/2007 | Chan et al. | |
| 2007/0299388 A1 | 12/2007 | Chan et al. | |
| 2008/0009811 A1 | 1/2008 | Cantor | |
| 2008/0108959 A1 | 5/2008 | Jung et al. | |
| 2008/0114298 A1* | 5/2008 | Cantor | A61M 37/0015 604/117 |
| 2008/0136874 A1 | 6/2008 | Tsukamura | |
| 2008/0245764 A1 | 10/2008 | Pirk et al. | |
| 2008/0287858 A1 | 11/2008 | Duan | |
| 2008/0312610 A1 | 12/2008 | Binks et al. | |
| 2008/0312669 A1 | 12/2008 | Vries et al. | |
| 2009/0017210 A1 | 1/2009 | Andrianov et al. | |
| 2009/0041810 A1 | 2/2009 | Andrianov et al. | |
| 2009/0198189 A1* | 8/2009 | Simons | A61M 37/0015 604/173 |
| 2009/0292254 A1 | 11/2009 | Tomono | |
| 2010/0221314 A1 | 9/2010 | Matsudo et al. | |
| 2010/0222743 A1 | 9/2010 | Frederickson et al. | |
| 2010/0256568 A1* | 10/2010 | Frederickson | A61M 37/0015 604/173 |
| 2011/0021996 A1 | 1/2011 | Lee et al. | |
| 2011/0028905 A1 | 2/2011 | Takada | |
| 2011/0059150 A1 | 3/2011 | Kendall et al. | |
| 2011/0160069 A1 | 6/2011 | Corrie et al. | |
| 2011/0223542 A1 | 9/2011 | Kendall | |
| 2011/0245776 A1 | 10/2011 | Kendall | |
| 2011/0276027 A1* | 11/2011 | Trautman | A61M 37/0015 604/506 |
| 2011/0288484 A1 | 11/2011 | Kendall et al. | |
| 2012/0027810 A1 | 2/2012 | Chen et al. | |
| 2012/0041412 A1 | 2/2012 | Roth et al. | |
| 2012/0083741 A1 | 4/2012 | Kendall | |
| 2012/0083762 A1 | 4/2012 | Kendall | |
| 2012/0109065 A1* | 5/2012 | Backes | A61M 37/0015 604/173 |
| 2012/0136312 A1* | 5/2012 | Terahara | A61B 5/150984 604/173 |
| 2012/0265141 A1* | 10/2012 | Kalpin | A61M 5/14276 604/131 |
| 2012/0277629 A1* | 11/2012 | Bernstein | A61B 5/1411 600/578 |
| 2012/0330250 A1 | 12/2012 | Kuwahara et al. | |

(56) References Cited

U.S. PATENT DOCUMENTS

| | | | |
|---|---|---|---|
| 2013/0079666 A1* | 3/2013 | Gonzalez-Zugasti | A61B 5/1411 600/583 |
| 2013/0131598 A1 | 5/2013 | Trautman et al. | |
| 2013/0150822 A1 | 6/2013 | Ross | |
| 2013/0158482 A1* | 6/2013 | Davis | A61B 5/150022 604/173 |
| 2013/0190794 A1 | 7/2013 | Kendall et al. | |
| 2013/0337150 A1 | 12/2013 | Biemans | |
| 2014/0243747 A1 | 8/2014 | Tokumoto et al. | |
| 2014/0257188 A1 | 9/2014 | Kendall et al. | |
| 2014/0276366 A1 | 9/2014 | Bourne et al. | |
| 2014/0276378 A1 | 9/2014 | Chen et al. | |
| 2014/0276474 A1 | 9/2014 | Ding et al. | |
| 2015/0057604 A1 | 2/2015 | Arami et al. | |
| 2015/0080844 A1 | 3/2015 | Donovan et al. | |
| 2016/0015952 A1 | 1/2016 | Omachi et al. | |
| 2016/0058697 A1 | 3/2016 | Kendall et al. | |
| 2016/0220803 A1 | 8/2016 | Kendall et al. | |
| 2016/0271381 A1 | 9/2016 | Falo, Jr. et al. | |
| 2016/0310412 A1 | 10/2016 | Tanoue et al. | |
| 2017/0014336 A1 | 1/2017 | Kuruma et al. | |
| 2017/0056637 A1 | 3/2017 | Unger et al. | |
| 2017/0065804 A1 | 3/2017 | Uemura | |
| 2017/0182301 A1 | 6/2017 | Kendall | |
| 2017/0282417 A1 | 10/2017 | Okano et al. | |
| 2017/0296465 A1 | 10/2017 | Yoshida et al. | |
| 2018/0161050 A1 | 6/2018 | Kendall | |
| 2018/0250503 A1 | 9/2018 | Enomoto et al. | |
| 2018/0263641 A1 | 9/2018 | Crichton et al. | |
| 2018/0264244 A1 | 9/2018 | Meliga et al. | |
| 2018/0326726 A1 | 11/2018 | Wang et al. | |
| 2019/0001109 A1 | 1/2019 | Kim et al. | |

FOREIGN PATENT DOCUMENTS

| | | |
|---|---|---|
| CN | 101297989 A | 11/2008 |
| EP | 0 139 286 B1 | 8/1991 |
| EP | 0 732 208 A1 | 9/1996 |
| EP | 1 695 734 B1 | 6/2008 |
| EP | 2 213 284 A1 | 8/2010 |
| EP | 2 327 419 A1 | 6/2011 |
| EP | 2 568 174 A1 | 3/2013 |
| EP | 2 835 147 A1 | 2/2015 |
| JP | 2003-127430 A | 5/2003 |
| JP | 2007-260889 A | 10/2007 |
| JP | 2010-071845 A | 4/2010 |
| JP | 2016-166769 A | 9/2016 |
| WO | 91/06571 A1 | 5/1991 |
| WO | 94/24281 A1 | 10/1994 |
| WO | 98/28037 A1 | 7/1998 |
| WO | 98/28038 A1 | 7/1998 |
| WO | 99/02694 A1 | 1/1999 |
| WO | 99/42564 A2 | 8/1999 |
| WO | 99/64580 A1 | 12/1999 |
| WO | 00/05339 A1 | 2/2000 |
| WO | 00/42215 A1 | 7/2000 |
| WO | 00/74763 A2 | 12/2000 |
| WO | 00/74764 A1 | 12/2000 |
| WO | 01/03361 A1 | 1/2001 |
| WO | 01/33614 A1 | 5/2001 |
| WO | 01/85207 A2 | 11/2001 |
| WO | 02/064193 A2 | 8/2002 |
| WO | 02/074173 A1 | 9/2002 |
| WO | 02/075794 A2 | 9/2002 |
| WO | 02/085446 A2 | 10/2002 |
| WO | 02/085447 A2 | 10/2002 |
| WO | 02/100476 A2 | 12/2002 |
| WO | 03/020359 A2 | 3/2003 |
| WO | 03/026732 A2 | 4/2003 |
| WO | 03/048031 A2 | 6/2003 |
| WO | 03/053258 A1 | 7/2003 |
| WO | 03/092785 A1 | 11/2003 |
| WO | 2004/000389 A2 | 12/2003 |
| WO | 2004/024224 A1 | 3/2004 |
| WO | 2005/049108 A2 | 6/2005 |
| WO | 2005/060621 A2 | 7/2005 |
| WO | 2005/069736 A2 | 8/2005 |
| WO | 2005/072360 A2 | 8/2005 |
| WO | 2005/072630 A1 | 8/2005 |
| WO | 2005/123173 A1 | 12/2005 |
| WO | 2006/055795 A1 | 5/2006 |
| WO | 2006/055799 A1 | 5/2006 |
| WO | 2006/101459 A1 | 9/2006 |
| WO | 2006/108185 A1 | 10/2006 |
| WO | 2006/116281 A2 | 11/2006 |
| WO | 2006/138719 A2 | 12/2006 |
| WO | 2007/002123 A2 | 1/2007 |
| WO | 2007/002521 A2 | 1/2007 |
| WO | 2007/012114 A1 | 2/2007 |
| WO | 2007/030477 A2 | 3/2007 |
| WO | 2007/054090 A1 | 5/2007 |
| WO | 2007/061781 A1 | 5/2007 |
| WO | 2007/061871 A1 | 5/2007 |
| WO | 2007/070004 A2 | 6/2007 |
| WO | 2007/080427 A2 | 7/2007 |
| WO | 2007/124411 A1 | 11/2007 |
| WO | 2007/127976 A2 | 11/2007 |
| WO | 2008/010681 A1 | 1/2008 |
| WO | 2008/011625 A2 | 1/2008 |
| WO | 2008/053481 A1 | 5/2008 |
| WO | 2008/069566 A1 | 6/2008 |
| WO | 2008/083209 A2 | 7/2008 |
| WO | 2008/091602 A2 | 7/2008 |
| WO | 2009/040548 A1 | 4/2009 |
| WO | 2009/066763 A1 | 5/2009 |
| WO | 2009/079712 A1 | 7/2009 |
| WO | 2009/081122 A1 | 7/2009 |
| WO | 2009/097660 A1 | 8/2009 |
| WO | 2009/140735 A1 | 11/2009 |
| WO | 2010/042996 A1 | 4/2010 |
| WO | 2010/071918 A1 | 7/2010 |
| WO | 2010/109471 A1 | 9/2010 |
| WO | 2011/105496 A1 | 9/2011 |
| WO | 2011/116388 A1 | 9/2011 |
| WO | 2012/122162 A1 | 9/2012 |
| WO | 2013/053022 A1 | 4/2013 |
| WO | 2013/055641 A1 | 4/2013 |
| WO | 2014/058746 A1 | 4/2014 |
| WO | 2015/034924 A1 | 3/2015 |
| WO | 2016/123665 A1 | 8/2016 |
| WO | 2016/143514 A1 | 9/2016 |
| WO | 2017/123652 A1 | 7/2017 |
| WO | 2018/119174 A1 | 6/2018 |

OTHER PUBLICATIONS

Albert et al., "Dendritic cells acquire antigen from apoptotic cells and induce class I-restricted CTLs," *Nature* 392:86-89, 1998.

Albert et al., "Tumor-specific killer cells in paraneoplastic cerebellar degeneration," *Nature Medicine* 4(11):1321-1324, 1998.

Anderson, "Cutaneous Microdialysis: Is it Worth the Sweat?," *Journal of Investigative Dermatology* 126:1207-1209, 2006.

Athanasopoulos et al., "Gene therapy vectors based on adeno-associated virus: Characteristics and applications to acquired and inherited diseases (Review)," *International Journal of Molecular Medicine* 6:363-375, 2000.

Australian Examination report No. 2 for standard patent application, dated Jan. 9, 2017, for Australian Application No. 2012323782, 4 pages.

Australian Patent Examination Report No. 1, dated Apr. 11, 2016, for Australian Application No. 2012323782, 3 pages.

Australian Patent Examination Report No. 1, dated Mar. 27, 2013, for Australian Application No. 2009212106, 5 pages.

Bachmann et al., "Dendritic cells process exogenous viral proteins and virus-like particles for class I presentation to CD8[+] cytotoxic T lymphocytes," *Eur. J. Immunol.* 26:2595-2600, 1996.

Camilli et al., "*Listeria monocytogenes* Mutants Lacking Phosphatidylinositol-specific Phospholipase C Are Avirulent," *J. Exp. Med.* 173:751-754, 1991.

(56) References Cited

OTHER PUBLICATIONS

Canadian Office Action, dated Apr. 23, 2015, for Canadian Application No. 2,749,347, 4 pages.
Canadian Office Action, dated Feb. 17, 2015, for Canadian Application No. 2,745,339, 4 pages.
Chinese 1$^{st}$ Office Action, dated Feb. 17, 2012, for Chinese Application No. 200980104635.3, 13 pages. (with English Translation).
Chinese 2$^{nd}$ Office Action, dated Sep. 24, 2012, for Chinese Application No. 200980104635.3, 9 pages. (with English Translation).
Chinese 3$^{rd}$ Office Action, dated Dec. 28, 2012, for Chinese Application No. 200980104635.3, 6 pages. (with English Translation).
Cormier et al., "Transdermal delivery of desmopressin using a coated microneedle array patch system," *Journal of Controlled Release* 97:503-511, 2004.
Cox et al., "Adjuvants—a classification and review of their modes of action," *Vaccine* 15(3):248-256, 1997.
Crichton et al., "The effect of strain rate on the precision of penetration of short densely-packed microprojection array patches coated with vaccine," *Biomaterials* 31(16):4562-4572, 2010.
Dreyer, "Microneedles: Microprocessing in Medicine," Final Presentation ENMA465 Project, May 10, 2004, URL=http://www.mse.umd.edu/undergrad/courses/ENMA465-project-results.html, 23 pages.
Extended European Search Report, dated Jul. 20, 2012, for European Application No. 09833918.7-1526, 9 pages.
Extended European Search Report, dated Sep. 26, 2014, for European Application No. 09707729.1-1508, 9 pages.
Extended European Search Report, dated Nov. 10, 2015, for European Application No. 12840561.0-1506, 11 pages.
Feng et al., "Molecular Biomarkers for Cancer Detection in Blood and Bodily Fluids," *Critical Reviews in Clinical Laboratory Sciences* 43(5-6):497-560, 2006.
Gao et al., "Priming of Influenza Virus-Specific Cytotoxic T Lymphocytes Vivo by Short Synthetic Peptides," *The Journal of Immunology* 147(10):3268-3273, 1991.
Gardeniers et al., "Silicon Micromachined Hollow Microneedles for Transdermal Liquid Transport," *Journal of Microelectromechanical Systems* 12(6):855-862, 2003.
Gill et al., "Coated microneedles for transdermal delivery," *Journal of Controlled Release* 117(2):227-237, 2007.
Gill et al., "Coating Formulations for Microneedles," *Pharmaceutical Research* 24(7):1369-1380, 2007.
International Preliminary Report on Patentability, dated Nov. 14, 2012, for International Application No. PCT/AU2011/000890, 6 pages.
International Preliminary Report on Patentability, dated Jun. 7, 2006, for International Application No. PCT/GB2005/000336, 9 pages.
International Preliminary Report on Patentability, dated Jun. 29, 2010, for International Application No. PCT/AU2008/001903, 7 pages.
International Search Report and Written Opinion, dated Mar. 7, 2016, for International Application No. PCT/AU2016/050056, 13 pages.
International Search Report and Written Opinion, dated Dec. 6, 2016, for International Application No. PCT/AU2016/050867, 20 pages.
International Search Report and Written Opinion, dated Dec. 22, 2016, for International Application No. PCT/AU2016/050907, 14 pages.
International Search Report and Written Opinion, dated Feb. 20, 2009, for International Application No. PCT/AU2008/001903, 11 pages.
International Search Report, dated Feb. 20, 2013, for International Application No. PCT/AU2012/001289, 13 pages.
International Search Report, dated Oct. 25, 2011, for International Application No. PCT/AU2011/000890, 4 pages.
Ito et al., "Evaluation of self-dissolving needles containing low molecular weight heparin (LMWH) in rats," *International Journal of Pharmaceutics* 349:124-129, 2008.
Ito et al., "Feasibility of microneedles for percutaneous absorption of insulin," *European Journal of Pharmaceutical Sciences* 29:82-88, 2006.
Ito et al., "Self-dissolving microneedles for the percutaneous absorption of EPO in mice," *Journal of Drug Targeting* 14(5):255-261, 2006.
Jondal et al., "MHC Class I-Restricted CTL Responses to Exogenous Antigens," *Immunity* 5:295-302, 1996.
Kay et al., "Viral vectors for gene therapy: the art of turning infectious agents into vehicles of therapeutics," *Nature Medicine* 7(1):33-40, 2001.
Kendall et al., "The mechanical properties of the skin epidermis in relation to targeted gene and drug delivery," *Biomaterials* 28:4968-4977, 2007.
Kuzu et al., "In vivo priming effect during various stages of ontogeny of an influenza A virus nucleoprotein peptide," *Eur. J. Immunol.* 23:1397-1400, 1993.
Kwon et al., "In Vitro Modeling of Transdermal PTH Delivery by Dissolving Micro-needle Patch," *34$^{th}$ Annual Meeting & Exposition of the Controlled Release Society*, Long Beach, California, USA, Jun. 5, 2007, 2 pages.
Kwon et al., "Rapid Intradermal Drug Delivery by a Dissolvable Micro-Needle Patch," *32$^{nd}$ Annual Meeting & Exposition of the Controlled Release Society*, Miami, Florida, USA, Jun. 18-22, 2005, 2 pages.
Kwon, "Acne Treatment by a Dissolvable Micro-Needle Patch," *33$^{rd}$ Annual Meeting & Exposition of the Controlled Release Society*, Vienna, Austria, Jul. 24, 2006, 2 pages.
Kwon, "In Vitro Evaluation of Transdermal Drug Delivery by a Micro-needle Patch," *31$^{st}$ Annual Meeting & Exposition of the Controlled Release Society*, Honolulu, Hawaii, USA, Jun. 12-16, 2004, 2 pages.
Lee et al., "Dissolving microneedles for transdermal drug delivery," *Biomaterials* 29:2113-2124, 2008.
Lin et al., "Silicon-Processed Microneedles," *IEEE Journal of Microelectromechanical Systems* 8(1):78-84, 1999.
Ma et al., "A PZT Insulin Pump Integrated with a Silicon Micro Needle Array for Transdermal Drug Delivery," *56$^{th}$ Electronic Components & Technology Conference*, San Diego, CA, May 30-Jun. 2, 2006, 5 pages.
Matriano et al., "Macroflux® Microprojection Array Patch Technology: A New and Efficient Approach for Intracutaneous Immunization," *Pharmaceutical Research* 19(1):63-70, 2002.
Mengaud et al., "Expression in *Escherichia coli* and Sequence Analysis of the Listeriolysin O Determinant of *Listeria monocytogenes*," *Infection and Immunity* 56(4):766-772, 1988.
Miyano et al., "Hydrolytic Microneedles as Transdermal Drug Delivery System," *14$^{th}$ International Conference on Solid-State Sensors, Actuators and Microsystems*, Lyon, France, Jun. 10-14, 2007, pp. 355-358.
Miyano et al., "Sugar Micro Needles as Transdermic Drug Delivery System," *Biomedical Microdevices* 7(3):185-188, 2005.
Moore et al., "Introduction of Soluble Protein into the Class I Pathway of Antigen Processing and Presentation," *Cell* 54:777-785, 1988.
Mukerjee et al., "Microneedle array for transdermal biological fluid extraction and in situ analysis," *Sensors and Actuators A* 114:267-275, 2004.
Oh et al., "Demonstration of Dose-controlled Delivery by Dissolvable Micro-needle Arrays," *34$^{th}$ Annual Meeting & Exposition of the Controlled Release Society*, Long Beach, California, USA, Jun. 5, 2007, 2 pages.
Oh et al., "Intradermal influenza vaccine delivery using skin-penetrating dissolvable vaccine microneedles," *AAPS Annual Meeting and Exposition*, San Antonio, Texas, USA, Oct. 29-Nov. 2, 2006, 1 page.
Palmer et al., "Streptolysin O: A Proposed Model of Allosteric Interaction between a Pore-Forming Protein and Its Target Lipid Bilayer," *Biochemistry* 37:2378-2383, 1998.
Park et al., "Biodegradable polymer microneedles: Fabrication, mechanics and transdermal drug delivery," *Journal of Controlled Release* 104:51-66, 2005.

(56) References Cited

OTHER PUBLICATIONS

Park et al., "Polymer Microneedles for Controlled-Release Drug Delivery," *Pharmaceutical Research* 23(5):1008-1019, 2006.
Park et al., "Towards the silicon nanowire-based sensor for intracellular biochemical detection," *Biosensors and Bioelectronics* 22:2065-2070, 2007.
Portnoy et al., "Capacity of Listeriolysin O, Streptolysin O, and Perfringolysin O to Mediate Growth of *Bacillus subtilis* within Mammalian Cells," *Infection and Immunity* 60(7):2710-2717, 1992.
Rossjohn et al., "Structure of a Cholesterol-Binding, Thiol-Activated Cytolysin and a Model of Its Membrane Form," *Cell* 89:685-692, 1997.
Schulz et al., "Peptide-induced antiviral protection by cytotoxic T cells," *Proc. Natl. Acad. Sci. USA* 88:991-993, 1991.
Silver et al., "Viscoelastic Properties of Young and Old Human Dermis: A Proposed Molecular Mechanism for Elastic Energy Storage in Collagen and Elastin," *J. Appl. Polym. Sci.* 86:1978-1985, 2002.
Stoeber et al., "Arrays of Hollow Out-of-Plane Microneedles for Drug Delivery," *Journal of Microelectromechanical Systems* 14(3):472-479, 2005.
Sullivan et al., "Minimally Invasive Protein Delivery with Rapidly Dissolving Polymer Microneedles," *Adv. Mater.* 20:933-938, 2008.
Tao et al., "A systematic study of dry etch process for profile control of silicon tips," *Microelectronic Engineering* 78-79:147-151, 2005.
Tsuchiya et al., "Development of Blood Extraction System for Health Monitoring System," *Biomedical Microdevices* 7(4):347-353, 2005.
Tyagi et al., "Molecular Beacons: Probes that Fluoresce upon Hybridization," *Nature Biotechnology* 14:303-308, 1996.
Vigna et al., "Lentiviral vectors: excellent tools for experimental gene transfer and promising candidates for gene therapy," *The Journal of Gene Medicine* 2:308-316, 2000.
Walther et al., "Viral Vectors for Gene Transfer: A Review of Their Use in the Treatment of Human Diseases," *Drugs* 60(2):249-271, 2000.
Wang et al., "Label-free hybridization detection of a single nucleotide mismatch by immobilization of molecular beacons on an agarose film," *Nucleic Acids Research* 30(12):e61, 2002. (9 pages).
Widera et al., "Effect of delivery parameters on immunization to ovalbumin following intracutaneous administration by a coated microneedle array patch system," *Vaccine* 24:1653-1664, 2006.
Wu et al., "Production of viral vectors for gene therapy applications," *Current Opinions in Biotechnology* 11:205-208, 2000.
Yuan et al., "Measuring microelastic properties of stratum corneum," *Colloids and Surfaces B: Biointerfaces* 48:6-12, 2006.
Zheng et al., "Multiplexed electrical detection of cancer markers with nanowire sensor arrays," *Nature Biotechnology* 23(10):1294-1301, 2005.
Zhou et al., "Liposome-Mediated Cytoplasmic Delivery of Proteins: An Effective Means of Accessing the MHC Class I-Restricted Antigen Presentation Pathway," *Immunomethods* 4:229-235, 1994.
U.S. Appl. No. 14/351,499, filed Apr. 11, 2014, Delivery Device.
U.S. Appl. No. 15/401,950, filed Jan. 9, 2017, Delivery Device.
U.S. Appl. No. 15/849,134, filed Dec. 20, 2017, Method of Delivering Material or Stimulus to a Biological Subject.
U.S. Appl. No. 15/760,869, filed Mar. 16, 2018, Microprojection Arrays With Microprojections Having Large Surface Area Profiles.
U.S. Appl. No. 15/762,913, filed Mar. 23, 2018, Microprojection Arrays With Enhanced Skin Penetrating Properties and Methods Thereof.
U.S. Appl. No. 15/942,895, filed Apr. 2, 2018, Device and Method for Coating Surfaces.
U.S. Appl. No. 16/622,092, filed Dec. 12, 2019, Quality Control of Substrate Coatings.
U.S. Appl. No. 16/636,467, filed Feb. 4, 2020, Compact High Mechanical Energy Storage and Low Trigger Force Actuator for the Delivery of Microprojection Array Patches (MAP).
U.S. Appl. No. 16/638,072, filed Feb. 25, 2020, Differential Coating of Microprojections and Microneedles on Arrays.

Boehm et al., "Inkjet printing for pharmaceutical applications," *Materials Today* 17(5):247-252, 2014.
Crichton et al., "The viscoelastic, hyperelastic and scale dependent behaviour of freshly excised individual skin layers," *Biomaterials* 32:4670-4681, 2011.
Desai et al., "Understanding release kinetics of biopolymer drug delivery microcapsules for biomedical applications," *Materials Science and Engineering B* 168:127-131, 2010.
European Search Report dated Sep. 10, 2018, for European Application No. 16746000.5, 3 pages.
Fernando et al., "Potent Immunity to Low Doses of Influenza Vaccine by Probabilistic Guided Micro-Targeted Skin Delivery in a Mouse Model,"*PLoS One* 5(4):e10266, 2010. (11 pages).
Garafalo et al., "Histamine release and therapy of severe dermatographism," *J. Allergy Clin. Immunol.* 68(2):103-105, 1981.
Henry et al., "Microfabricated Microneedles: A Novel Approach to Transdermal Drug Delivery," *Journal of Pharmaceutical Sciences* 87(8):922-925, 1998.
International Preliminary Report on Patentability dated Feb. 4, 2020 for International Application No. PCT/AU2018/050810, 9 pages.
International Search Report dated Jul. 30, 2018, for International Application No. PCT/AU2018/050298, 6 pages.
International Search Report dated Sep. 13, 2018, for International Application No. PCT/AU2018/050847, 4 pages.
International Search Report dated Nov. 8, 2018 for International Application No. PCT/AU2018/050810, 8 pages.
International Search Report dated Aug. 1, 2018, for International Application No. PCT/AU2018/050586, 4 pages.
Ma et al., "Coating solid dispersions on microneedles via a molten dip coating method: development and in vitro evaluation for transdermal delivery of a water insoluble drug," *J Pharm Sci* 103(11):3621-3630, 2014 (HHS Public Access Author manuscript, available in PMC Nov. 1, 2015)(21 pages).
McAllister et al., "Microfabricated needles for transdermal delivery of macromolecules and nanoparticles: Fabrication methods and transport studies," *PNAS* 100(24):13755-13760, 2003.
Meléndez et al., "Thermal Inkjet Application in the Preparation of Oral Dosage Forms: Dispensing of Prednisolone Solutions and Polymorphic Characterization by Solid-State Spectroscopic Techniques," *Journal of Pharmaceutical Sciences* 97(7):2619-2636, 2008.
Radulescu et al., "Uniform Paclitaxel-Loaded Biodegradable Microspheres Manufactured by Ink-Jet Technology," *Proc., the Winter Symposium and 11th International Symposium on Recent Advantages in Drug-Delivery Systems, Controlled Release Society*, Salt Lake City, Utah, 2003, 5 pages.
Sandler et al., "Inkjet Printing of Drug Substances and Use of Porous Substrates-Towards Individualized Dosing," *Journal of Pharmaceutical Sciences* 100(8):3386-3395, 2011.
Scoutaris et al., "ToF-SIMS analysis of chemical heterogenities in inkjet micro-array printed drug/polymer formulations," *J Mater Sci: Mater Med* 23:385-391, 2012.
Tarcha et al., "The Application of Ink-Jet Technology for the Coating and Loading of Drug-Eluting Stents," *Annals of Biomedical Engineering* 35(10):1791-1799, 2007.
Wu et al., "Solid free-form fabrication of drug delivery devices," *Journal of Controlled Release* 40:77-87, 1996.
U.S. Appl. No. 17/089,446, filed Nov. 4, 2020, Delivery Device.
U.S. Appl. No. 16/896,387, filed Jun. 9, 2020, Delivery Device.
U.S. Appl. No. 17/326,064, filed May 20, 2021, Method of Delivering Material or Stimulus to a Biological Subject.
U.S. Appl. No. 17/241,927, filed Apr. 27, 2021, Microprojection Arrays With Enhanced Skin Penetrating Properties and Methods Thereof.
U.S. Appl. No. 17/323,671, filed May 18, 2021, Quality Control of Substrate Coatings.
Australian Examination Report No. 1 dated Oct. 9, 2020 for Australian Application No. 2016333148, 5 pages.
Chinese Office Action dated Jan. 11, 2021 for Chinese Application No. 201880036675.8, 31 pages. (w/ machine translation).
Communication pursuant to Article 94(3) EPC, dated Jan. 19, 2021, for European Application No. 16 746 000.5, 4 pages.

(56) References Cited

OTHER PUBLICATIONS

Extended European Search Report dated Nov. 30, 2020 for European Application No. 18 77 6793, 10 pages.
Extended European Search Report dated Feb. 15, 2021 for European Application No. 18 81 6698, 8 pages.
Fernando et al., "Safety, tolerability, acceptability and immunogenicity of an influenza vaccine delivered to human skin by a novel high-density microprojection array patch (NanopatchTM)," Vaccine 36:3779-3788, 2018.
Fernando et al., "Influenza nucleoprotein DNA vaccination by a skin targeted, dry coated, densely packed microprojection array (Nanopatch) induces potent antibody and CD8+ T cell responses," Journal of Controlled Release 237:35-41, 2016.
International Search Report dated May 25, 2020 for International Application No. PCT/AU2020/050296, 6 pages.
Muller et al., "High-density microprojection array delivery to rat skin of low doses of trivalent inactivated poliovirus vaccine elicits potent neutralising antibody responses," Scientific Reports 7:12644, 2017. (10 pages).
Ng et al., "Potent response of QS-21 as a vaccine adjuvant in the skin when delivered with the Nanopatch, resulted in adjuvant dose sparing," Scientific Reports 6:29368, 2016. (12 pages).
Scoutaris et al., "Current Trends on Medical and Pharmaceutical Applications of Inkjet Printing Technology," Pharm Res. 33:1799-1816, 2016.

\* cited by examiner

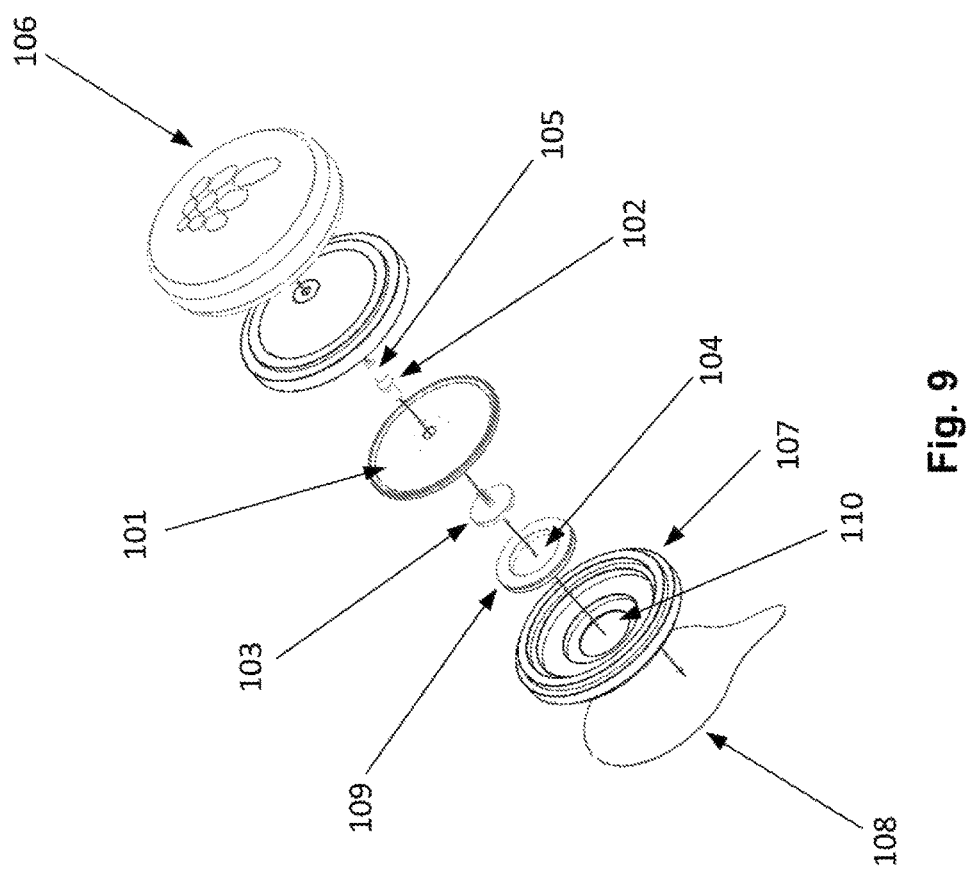

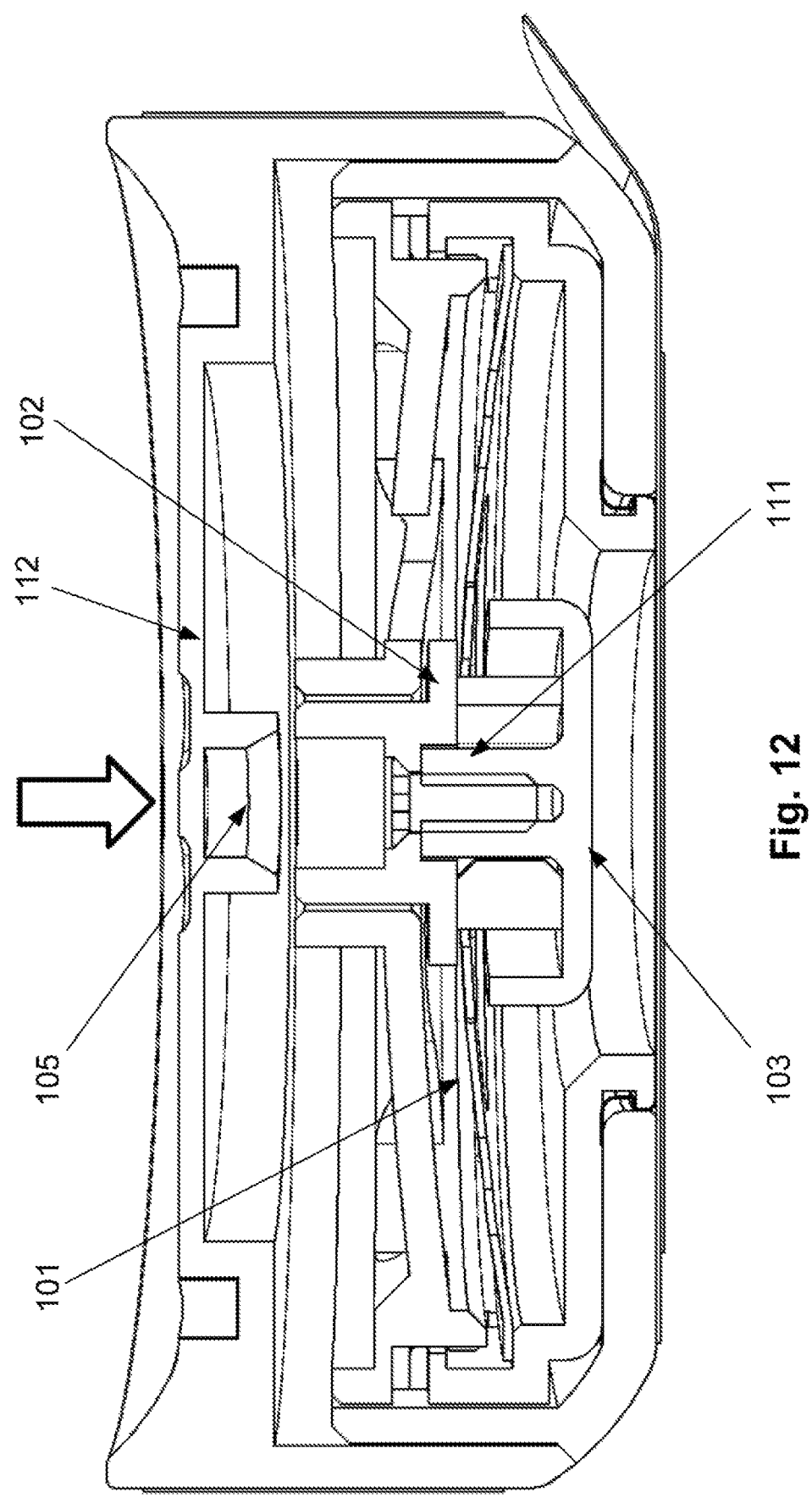

MICROPROJECTION ARRAY APPLICATOR AND METHOD

FIELD OF THE INVENTION

The present invention relates to applicators for administering microprojection arrays to skin and methods of administering microprojection arrays, in particular the administration of high density microprojection arrays.

BACKGROUND OF THE INVENTION

Recently, new methods of delivering drugs and other bioactive materials have been developed that are more convenient, provide superior efficacy or enhanced in performance compared to intramuscular and intradermal injection. Intradermal injection is limited by cross-contamination through needle-stick injuries in health workers, injection phobia from a needle and syringe, and the inability for needle and syringe methodology to target key cells in the outer skin layers.

US Patent Publication No. 2009/0198189 describes a device for applying a microneedle array to a skin surface in which the device is comprised of a base which defines a skin contacting plane, a microneedle array and a connecting member having a portion affixed to the base through a hinge and another portion affixed to the microneedle array.

US Patent Publication No. 2011/0276027 also describes an applicator for microneedles in which the applicator comprises an energy-storing element which upon application of force cause the compressed element to extend or transition from a first to a second configuration releasing the stored energy to deploy a member which is configured to hold a microneedle array.

U.S. Pat. No. 8,540,672 describes an applicator includes a housing, a slidably disposed applicator plate, and a compression spring. The applicator plate is moveable between a retracted position and a deployed position, and has an engaging surface suitable for mashing up against a microneedle patch and pressing it against a skin surface. A docking system transfers the microneedle patch from a support to the applicator without requiring a user to handle the microneedle patch directly. Once mounted in the applicator, the microneedle patch is deployed against a skin surface of a patient for delivery of a desired agent via a microneedle array contained on the patch.

US Patent Publication No. 2008/0009811 describes an applicator capable of sensing a controlled distance from a skin surface and propelling a microneedle array across this distance and into the skin surface is disclosed. A method of applying a microneedle array to a skin surface by placing the microneedle array a predetermined distance away from the skin surface and propelling the microneedle array into the skin surface is disclosed.

WO 2014/058746 describes an applicator for applying a microneedle device to a skin surface. The applicator can include a microneedle device, a housing, and a connecting member. The connecting member can be configured to allow the microneedle device to move between: (i) a first position in which at least a portion of the microneedle device extends beyond the housing; and (ii) a second position in which the microneedle device is recessed within the housing when a threshold application force is applied to the microneedle device in a direction substantially perpendicular with respect to the microneedle device.

Despite the development of numerous devices for the application of microprojection and microneedle arrays there remain difficulties in devising a device and method for the arrays to overcome the natural elasticity of the skin and penetrating the skin to deliver the required drug dosage while maintaining comfort and ease of use for the patient. This is especially true when the microprojections arrays have a large number of densely packed microprojections in a small area array. The present invention is designed to achieve tolerable penetration for high density projection arrays >5,000 projections/cm$^2$ (flying patch and low mass). The prior art does not disclose an applicator for microprojection arrays or a method of application of microprojection arrays to the skin where high velocity can be achieved to deliver the high density microprojection array such that the patient does not feel discomfort. The applicators and methods of the present invention can deliver microprojection arrays that have a high density of projections in a small area while also having a low mass at high velocities to a patient's skin. The applicators and methods of the present invention perform such that the application of the microprojection array is tolerable to the patient.

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

SUMMARY OF THE INVENTION

The present invention relates to microprojection array applicators that provide application of microprojection arrays to skin for the delivery of substances, in particular microprojections arrays having a large number of densely packed microprojections in a small area array. The present invention also relates to methods of using the microprojection array applicators for applying arrays to the skin of a subject. The applicators or devices of the present invention may be constructed of one or more cantilevered rings or domes placed within a housing or sterile barrier such that when activated the applicator is activated the cantilevered ring applies force which in turn imparts an acceleration to a microprojection array which is projected into the skin. The applicators or devices of the present invention may be constructed of a single or multiple cantilevered rings. In one embodiment a single cantilevered ring is encased in a protective housing in which the housing has an internal face and an external face wherein the external face has a flexible section that when collapsed actuates the device. The force applied to the collapsible section is transmitted to the cantilevered rings which transition from a primed state to a fired state thereby activating the device The device may have a patch guide having a proximal and distal end where the proximal end interfaces with the internal face of the applicator housing such that when the flexible section of the external face of the housing is collapsed the patch guide is forced downward and interfaces with a cantilevered ring (or directly onto the array) which has an opening through which the patch guide passes and where the cantilevered ring is activated by the patch guide. Once activated the cantilevered ring is fired and propels the back of the microprojection array toward the skin. In some embodiments the device also contains a skin contact membrane which may be held in place by a skin contact applicator base that attaches to the housing such that when the microprojection array is propelled forward by the cantilevered ring, the microprojection array pierces the skin contact membrane prior to the microprojection array entering the skin. In another embodiment, two cantilevered rings are placed within a protective housing where the housing has a finger detent for actuating the device. The microprojection array applicators or devices may apply the microprojection device to the skin either by having the microprojection array remaining attached to the applicator or by uncoupling the microprojection array from the device such that the array is propelled from the device and "flies" through some distance between the applicator and the skin such that the applicator and array are not coupled when the array penetrates the skin.

The devices of the present invention may be multiple use devices or single use devices or disposable devices. The present invention relates to microprojection applicators in which a membrane may be introduced between the microprojection array and the skin surface to which the array is applied. The device may also comprise a cover or label which is attached to the membrane that can be releasably detached from the membrane. The cover may serve as a sterile barrier to protect the membrane and/or the microprojection array.

The present invention also relates to methods of applying microprojection arrays to the skin. Methods for applying a microprojection array to skin may comprise using the applicators of the present invention by depressing the collapsible section of the device housing thereby activating a first dome which translates its force through a second dome thereby releasing the microprojection array into the skin. Certain embodiments of the device have a membrane covering the microprojection array which may be further covered at least partially by a cover or label which is removed prior to activation of the device.

The present invention relates to devices for applying a microprojection array to a skin surface which have a housing having an upper and lower portion and having an internal face and an external face wherein the external face has a flexible section that when collapsed actuates the device; a patch guide having a proximal and distal end wherein the proximal end interfaces with the internal face of the housing such that when the flexible section of the external face of the housing is collapsed the patch guide is forced downward; a cantilevered ring having an opening through which the patch guide passes and wherein the cantilevered ring is activated by the patch guide; a microprojection array that is contacted by the cantilevered ring when the ring is activated; optionally a skin contact membrane; and optionally a skin contact applicator base that attaches to the housing.

The present invention relates to devices where the flexible section of the housing is in the upper portion of the housing.

The present invention relates to devices where the flexible section of the housing is in the lower portion of the housing.

The present invention relates to devices where the device further comprise a membrane support which interfaces with the skin contact applicator base and holds the skin contact membrane in place.

The present invention relates to devices where the devices further comprise a cover to at least partially cover the skin contact applicator base.

The present invention relates to devices where the cover keeps the device sterile and prevents fluids from getting in the device.

The present invention relates to devices where the device further comprises a stopping mechanism to prevent the microprojection array from flying out of the device if the device is unintentionally triggered.

The present invention relates to devices where the microprojection array remains attached to the device and can be removed from the skin when device is pulled away from the skin.

The present invention relates to devices where the stopping mechanism is part of the patch guide.

The present invention relates to devices where the microprojection array is a high density array.

The present invention relates to devices where the first external housing has a finger detent for actuating the device.

The present invention relates to devices where the flexible section is off-center.

The present invention relates to devices where the microprojection array has a density of from 5000 to 20,000 projections per $cm^2$.

The present invention relates to devices where the cantilevered rings achieve a velocity of between about 20 to about 50 meters/second when activated.

The present invention relates to devices where the device is a single use device.

The present invention relates to devices where the device is a disposable device.

The present invention relates to devices where the disposal of the device reduces contaminated waste incineration by using materials that emit a minimum of toxins upon incineration and reduce volume of packaging and device.

The present invention relates to devices where the membrane is made of a polymer film.

The present invention relates to devices where the polymer film is from about 2 to about 20 μm thick.

The present invention relates to devices where the polymer film includes a substance either coated onto the polymer film or with in the polymer film.

The present invention relates to devices where the substance has a therapeutic or prophylactic effect.

The present invention relates to devices where the substance is a therapeutic agent to assist in wound healing.

The present invention relates to devices where the cover is a foil seal.

The present invention relates to devices where the substance is a desiccant.

The present invention relates to devices where a desiccant is included inside the device.

The present invention relates to devices where a desiccant is included in the housing and/or molded parts of the device.

The present invention relates to devices where the device also removes the microprojection array from the skin after the microprojection array penetrates the skin.

The present invention relates to devices where the microprojection array can be releasably detached from the device.

The present invention relates to devices where the microprojection array has a mass from about 0.1 grams to about 0.5 grams.

The present invention relates to devices where the microprojection array has a mass from about 0.3 grams.

The present invention relates to devices where the internal portion of the device is sterile.

The present invention relates to devices where the housing forms a sealed sterile barrier and once used the device can be disassembled without contaminated features contacting the user.

The present invention relates to devices where the device further comprises a triggering device that provides a force multiplier.

The present invention relates to devices where the cantilevered ring is comprised of stainless steel.

The present invention relates to devices where the cantilevered ring has slots other than the hole through which the patch guide passes.

The present invention relates to devices where the cantilevered ring is not slotted at the top or the bottom of the cantilevered ring.

The present invention relates to devices where the cantilevered ring is from about 0.5 to about 1.5 mm in height.

The present invention relates to devices where the cantilevered ring is symmetrical.

The present invention relates to devices where the cantilevered ring includes a capacitive material.

The present invention relates to devices where the capacitive material is rubber.

The present invention relates to devices where the capacitive material is in the shape of an O-ring.

The present invention relates to methods for applying a microprojection array to skin by providing the applicators of the present invention and placing the applicator on the skin surface such that the bottom of the applicator housing is in contact with the skin surface and collapsing the flexible section of the housing, thereby pushing down on the patch guide and activating the cantilevered ring which strikes the back of the microprojection array and pushes the microprojection array through the membrane and into the skin surface.

The present invention relates to methods for applying a microprojection array where the microprojection array is released from the device and travels through a space before entering the skin.

The present invention relates to methods for applying a microprojection array by providing the applicators of the present invention and removing the cover; placing the applicator on a skin surface such that the bottom of the applicator housing is in contact with the skin surface; and collapsing the flexible section of the housing of the applicator, thereby pushing down on the patch guide and activating the cantilevered ring which strikes the back of the microprojection array and propels the microprojection array through the membrane and into the skin.

The present invention relates to methods for applying a microprojection array where the microprojection array is released from the device and travels through a space before entering the skin.

The present invention relates to methods for applying a microprojection array where the microprojection array attains a velocity of greater than about 20 m/s.

The present invention relates to methods for applying a microprojection array where the microprojection array attains a velocity of greater than about 25 m/s.

The present invention relates to methods for applying a microprojection array where the microprojection array attains a velocity of from about 20 to about 50 m/s.

The present invention relates to methods for applying a microprojection array where the microprojection array attains a velocity of from about 20 to about 26 m/s.

The present invention relates to methods for applying a microprojection array where the cantilevered ring strikes the back of the microprojection array at the cantilevered ring's maximum velocity.

The present invention relates to devices where for applying a microprojection array to a skin surface having a housing having a flexible section that when collapsed actuates the device; a first cantilevered ring; a second cantilevered ring; a microprojection array; a skin contact membrane; and a skin contact applicator base that attaches to the housing.

The present invention relates to devices where the orientation of the second cantilevered ring relative to the first cantilevered ring is inverted.

The present invention relates to devices where the first cantilevered ring is stacked upon the second cantilevered ring.

The present invention relates to devices where the first cantilevered ring has a lower trigger force than the second cantilevered ring.

The present invention relates to devices where the first cantilevered ring has a primed position and a fired position and the second cantilevered ring has a primed position and a fired position.

The present invention relates to devices where when the housing is collapsed the housing actuates the device and the first cantilevered ring moves from its primed position to its fired position thereby hitting the second cantilevered ring which in turn hits the microprojection array thereby propelling the microprojection array forward through the skin contact membrane.

The present invention relates to devices where the first cantilevered ring has a lower trigger force than the second cantilevered ring.

The present invention relates to devices where the first cantilevered ring hits the second cantilevered ring when the first cantilevered ring is at its maximum velocity by optimizing the spacing between the rings.

The present invention relates to devices where the second cantilevered ring hits the microprojection array when the second cantilevered ring is at its maximum velocity.

The present invention relates to devices where the microprojection array has a density of from 5000 to 20,000 projections per $cm^2$.

The present invention relates to devices where the first cantilevered ring's maximum velocity is between about 20 to about 50 meters/second when activated.

The present invention relates to devices where the second cantilevered ring's maximum velocity is between about 20 to about 50 meters/second when activated.

The present invention relates to devices where the microprojection array achieves a velocity of between about 20 to about 50 meters/second.

The present invention relates to methods for applying a microprojection array by providing applicators of the present invention; placing the applicator on a skin surface such that the bottom of the applicator housing is in contact with the skin surface; and collapsing the flexible section of the applicator housing, thereby actuating the device such that the first cantilevered ring moves from its primed position to its fired position thereby hitting the second cantilevered ring which in turn hits the microprojection array thereby propelling the microprojection array forward through the skin contact membrane.

The present invention relates to methods for applying a microprojection array where the first cantilevered ring has a lower trigger force than the second cantilevered ring.

The present invention relates to methods for applying a microprojection array where the first cantilevered ring hits the second cantilevered ring when the first cantilevered ring is at its maximum velocity.

The present invention relates to methods for applying a microprojection array where the second cantilevered ring hits the microprojection array when the second cantilevered ring is at its maximum velocity.

The present invention relates to methods for applying a microprojection array where the microprojection array has a density of from 5000 to 20,000 projections per $cm^2$.

The present invention relates to methods for applying a microprojection array where the first cantilevered ring's maximum velocity is between about 20 to about 50 meters/second when activated.

The present invention relates to methods for applying a microprojection array where the second cantilevered ring's maximum velocity is between about 20 to about 50 meters/second when activated.

The present invention relates to methods for applying a microprojection array where the microprojection array achieves a velocity of between about 20 to about 50 meters/second.

The present invention relates to devices for applying a microprojection array to a skin surface having a housing having a flexible section that when collapsed actuates the device; two or more cantilevered rings having a first and a last ring, wherein the cantilevered rings are stacked such that when the device is actuated the first ring is fired such that each successive ring is contacted by the preceding ring; a microprojection array wherein the last ring contacts the microprojection array; a skin contact membrane; and a skin contact applicator base that attaches to the housing.

The present invention relates to devices for applying a microprojection array to a skin surface having a housing having a flexible section and a base defining an opening that in use is provided in contact with the skin surface; a patch guide movably mounted within the housing, wherein the patch guide supports a microprojection array in use; and a biasing member supported by the housing and movable from a first position to a second position upon deformation of the flexible section, wherein the biasing member urges the microprojection array into engagement with a skin surface through the opening.

The present invention relates to devices where the biasing member is a cantilevered ring.

The present invention relates to devices where the deformation of the flexible section causes the biasing member to be urged from the first position to the second position by a part of the patch guide.

The present invention relates to devices where the deformation of the flexible section causes the biasing member to be urged from the first position to the second position by a part of the housing.

The present invention relates to devices for applying a microprojection array to a skin surface having a housing having a base defining an opening that in use is provided in contact with the skin surface; a patch guide movably mounted within the housing, wherein the patch guide supports a microprojection array in use; a trigger; a skin contact membrane provided in the opening; and a biasing member supported by the housing and movable from a first position to a second position upon activation of the trigger, wherein the biasing member urges the microprojection array through the skin contact membrane and into engagement with a skin surface through the opening.

The present invention relates to devices where the biasing member is a cantilevered ring.

The present invention relates to devices where the trigger is provided by a part of the patch guide.

Array as used herein refers to devices that include one or more structures such as microprojections capable of piercing the stratum corneum to facilitate transdermal delivery of therapeutic agents through or to the skin.

Microprojections, as used herein, refer to the specific microscopic structures associate with the array that are capable of piercing the stratum corneum to facilitate transdermal delivery of therapeutic agents through or to the skin. Microprojections may include needle or needle-like structures, micro-pins as well as solid projections. The microprojections may have any shape including but not limited to pyramidal rectangular, square, or oblong.

The term dome and cantilevered ring are used interchangeably and refer to a component of the applicator that has a concave shape and is an energy storing element. Examples of various cantilevered rings and domes are shown in FIG. 10.

The term patch and microprojection array are used interchangeable and refer to a device that includes one or more structures capable of piercing the stratum corneum to facilitate the transdermal delivery of prophylactic or therapeutic agents. The structures may be microneedles, microprojections, microblades or any other structure capable of penetrating the skin.

BRIEF DESCRIPTION OF THE FIGURES

FIG. 9 is an exploded view of one embodiment of the microprojection array applicator of the present invention showing the various parts of the applicator.

FIG. 12 is a cut away view of one embodiment of the applicator in which the top portion of the applicator has a deformable section.

DETAILED DESCRIPTION OF THE INVENTION

Commercial applicators for delivering microprojection arrays to the skin of patients may cause pain or discomfort to patients as the combined mass and speed of the array and mechanism for delivering the array to the skin can bruise the patient. This is especially true in the delivery of microprojection arrays having a large number of densely packed projections in a small area patch. The applicators and methods of the present invention can deliver microprojection arrays, which have a high density of projections in a small area while also having a low mass, at high velocities to a patient's skin. The applicators and methods of the present invention perform in such a way that the application of the microprojection array is tolerable to the patient such that the patient is not bruised or discomforted by the application of the microprojection array.

The present invention relates to microprojection array applicators that provide application of microprojection arrays to the skin for the delivery of substances in particular the delivery of vaccine antigens. The present invention also relates to methods of using the microprojection array applicators for applying microprojection arrays to the skin of a subject. The applicators and methods of the present invention are especially useful for the delivery of high density microprojection arrays to the skin surface. The applicators and methods of the present invention are also useful for the delivery of high density microprojection arrays at a high rate of speed to the skin surface. The present invention is designed to achieve tolerable penetration for high density, low mass microprojection arrays (>5,000/cm$^2$) that are delivered to the skin at high velocities.

Figure 1:
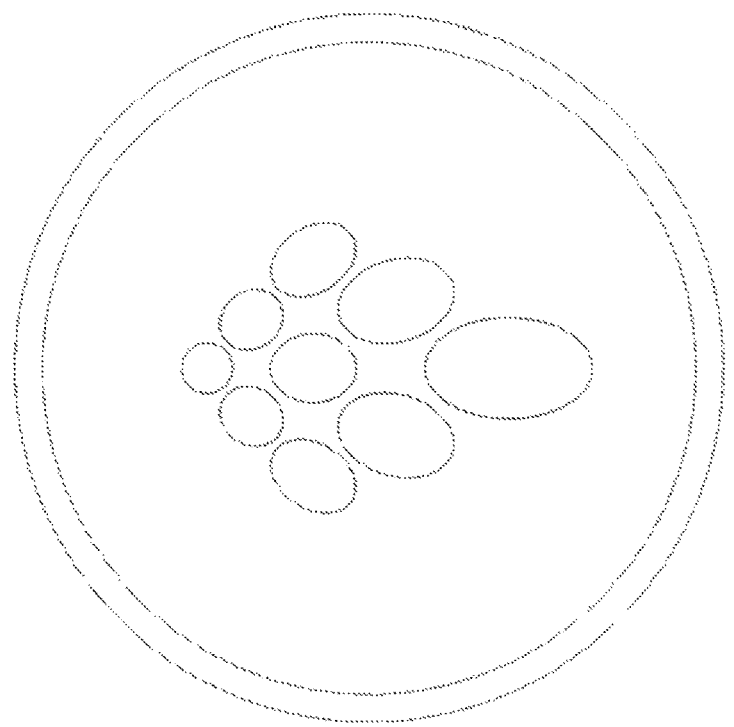
FIG. 1 is a top view of one embodiment of the microprojection array applicator of the present invention.
Figure 2:
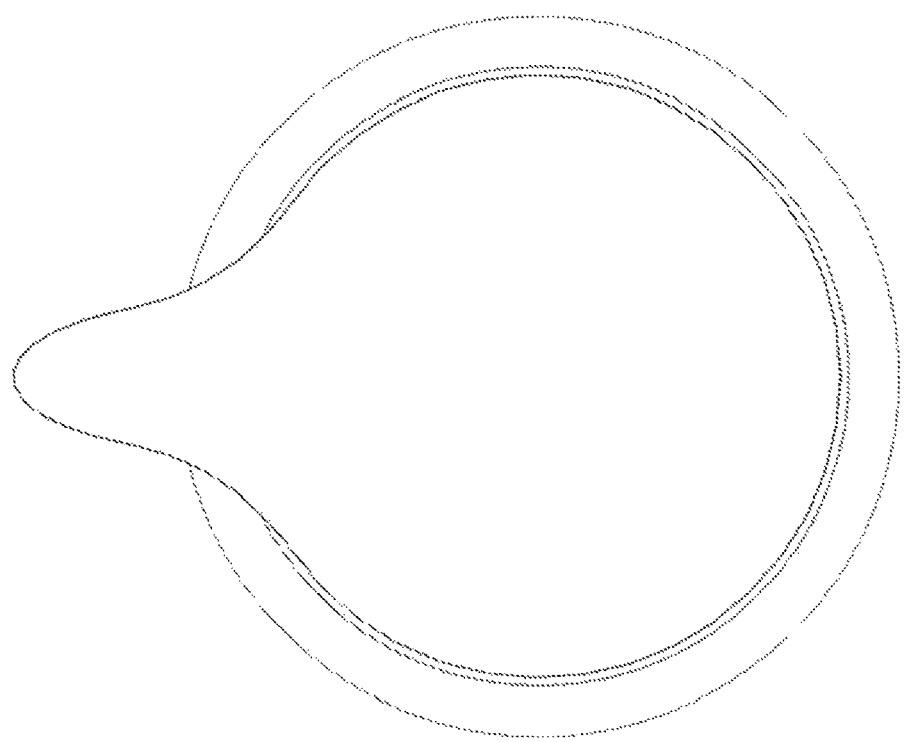
FIG. 2 is a bottom view of one embodiment of the microprojection array applicator of the present invention where the applicator bottom is covered by a foil covering.
Figure 3:
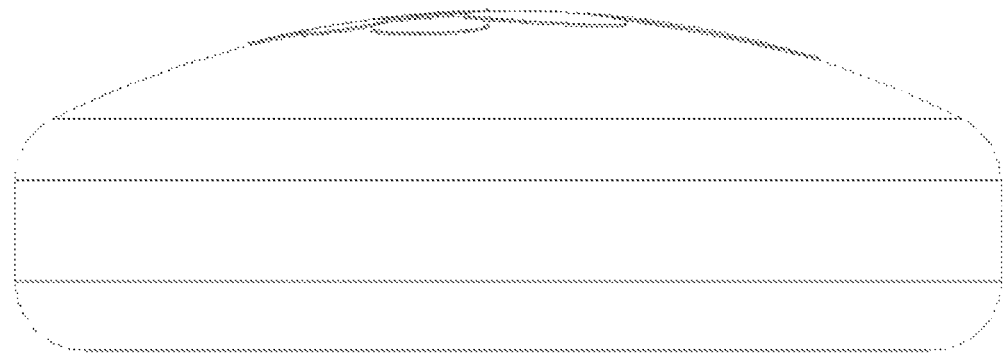
FIG. 3 is a side view of one embodiment of the microprojection array applicator of the present invention.
Figure 4:
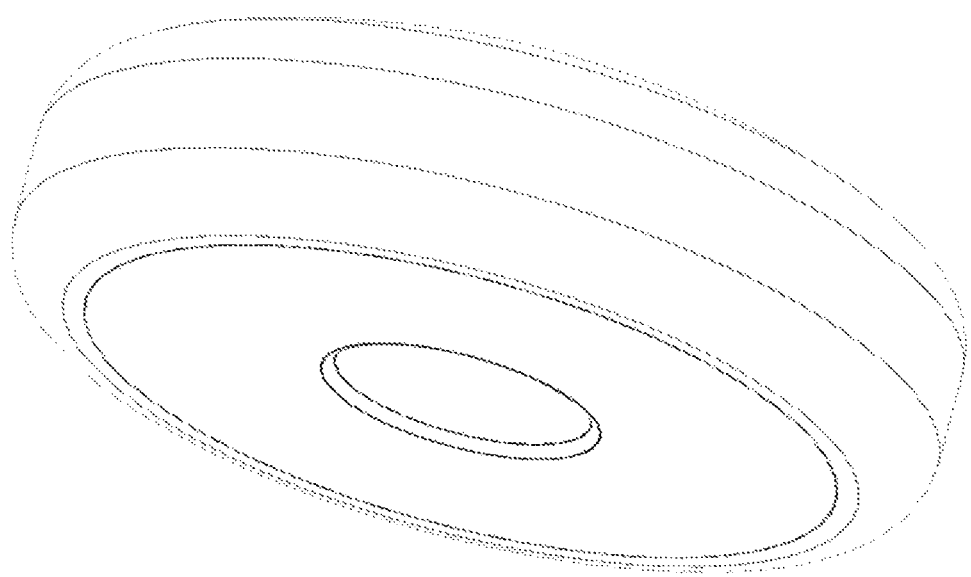
FIG. 4 is a bottom angled view of one embodiment of the microprojection array applicator of the present invention showing the membrane in the bottom hole of the applicator.

The applicators of the present invention may be comprised of a sterile housing which contains one or more cantilevered rings and one or more microprojection array(s). The housing may preferably be made of plastic or a metallic material such as steel or aluminium or a fibrous paper based material or a laminate including any of these materials. FIGS. 1 and 2 show the top and bottom perspective of one embodiment of the microprojection array applicator of the present invention, respectively. In FIG. 2, the bottom of the microprojection array applicator is covered with a foil sheet to protect the membrane and to keep the device sterile. FIG. 3 shows a side view of one embodiment of the microprojection array applicator of the present invention, while FIG. 4 shows an angled view of the bottom of one embodiment of the microprojection array applicator of the present invention without the foil covering thus showing the membrane covering the hole in the bottom of the device. The housing encompasses the inner workings of the applicator. The housing has an upper and lower section. The housing may have a collapsible section which acts as a trigger to activate the cantilevered rings(s) or dome(s). The collapsible section or sections of the housing may be on upper section of the device as in FIG. 5 and FIG. 12 or incorporated into the bottom of the housing as in FIG. 11 where deformable sections (112) are indicated. Preferably the flexible or collapsible section of the housing is actuated through a force applied by hand such that application of the microprojection array is comfortable to both the patient and the person activating the applicator. In one embodiment of the applicator of the present invention the force is applied to the applicator in a fashion that is substantially perpendicular to the skin to which the microprojection array is applied such that the force travels down through the cantilevered ring(s). Alternatively, the activation force could be applied in a direction substantially parallel to the skin by a mechanism that may be actuated between the thumb and forefinger. The mechanism by which the applicator is activated should not cause discomfort to the patient. The amount of force applied to activate the applicator may be about 2 newtons or about 3 newtons or about 4 newtons or about 5 newtons or about 6 newtons or about 7 newtons or about 8 newtons or about 9 newtons or about 10 newtons or about 11 newtons or about 12 newtons or about 13 newtons or about 14 newtons or about 15 newtons or about 16 newtons or about 17 newtons or about 18 newtons or about 19 newtons or about 20 newtons or about 21 newtons or about 22 newtons or about 23 newtons or about 24 newtons or about 25 newtons. The amount of force applied may be between about 2 to about 25 newtons or about 5 to 25 newtons or about 10 to 25 newtons or from about 15 to 25 newtons or from about 20 to 25 newtons. Alternatively, the triggering of the applicator may be effectuated by an indirect input such a lever or other force multiplier that would permit higher triggering forces. In preferred embodiments of the devices of the present invention the triggering of the device is accomplished by an off center trigger. If the cantilevered ring is triggered centrally a much larger force is required to initiate the snap of the cantilevered ring and will increase patient discomfort. Domes and inverted cones do not trigger symmetrically but rather as a wave form deformation.

The applicator of the present invention may be comprised of an outer housing which contains within it one or more cantilevered rings for translating a force through the device to deliver one or more microprojection arrays to the skin. The cantilevered rings and the outer housing of the applicator may have a concave shape. This concave shape can be a single curve or a complex curve that has designed within it a deformation zone. The cantilevered rings may be made of steel, carbon fibre, plastic or a composite of these materials. The diameter of the applicator device as well as the cantilevered rings may vary from application to application. The size of the device as well as the shape of the base of the device may depend on the application such as whether the patient is pediatric or geriatric or whether the patient is slim or obese. Moreover the area of application such as forearm or deltoid might dictate the shape of the device so that the applicator may fit more easily against the skin of the patient. The cantilevered rings used in the microprojection array applicator may have diameters from about 25 to 80 mm or from about 30 to 80 mm or from about 35 to 80 mm or from about 40 to 80 mm or from about 45 to 80 mm or from about 50 to 80 mm or from about 55 to 80 mm or from about 60 to 80 mm or from about 30 to 70 mm or from about 35 to 70 mm or from about 40 to 70 mm or from about 45 to 70 mm or from about 50 to 70 mm or from about 25 to 60 mm or from about 30 to 60 mm or from about 35 to 60 mm or from about 40 to 60 mm or from about 45 to 60 mm or from about 25 to 50 mm or from about 30 to 50 mm or from about 35 to 50 mm or from about 40 to 50 mm. The height of the dome(s) may range from about 0.5 to about 10 mm or from about 0.5 to about 9 mm or from about 0.5 to about 8 mm or from about 0.5 to about 7 mm or from about 0.5 to about 6 mm or from about 0.5 to about 5 mm or from about 0.5 to about 4 mm or from about 0.5 to about 3 mm or from about 0.5 to about 2 mm or from about 0.5 to about 1.5 mm or from about 0.5 mm to about 10 mm or from about 1.5 to about 10 mm or from about 1.5 to about 9 mm or from about 1.5 to about 8 mm or from about 1.5 to about 7 mm or from about 1.5 to about 6 mm or from about 2.5 to about 10 mm or from about 2.5 to about 9 mm or from about 2.5 to about 8 mm or from about 2.5 to about 7 mm or from about 2.5 to about 6 mm. The distance between multiple cantilevered rings used in the devices depends on the dome height and the distance the dome will travel but may be from about 1.5 to about 8 mm or from about 1.5 to about 7 mm or from about 1.5 to about 6 mm or from about 2.5 to about 8 mm or from about 2.5 to about 7 mm or from about 2.5 to about 6 mm. The cantilevered ring(s) may have various shapes which may be either symmetrical or asymmetrical. Moreover, the domes may be solid or may have holes in them or may have segments which have been removed from a solid dome (See FIG. 10 for examples of the various dome configurations). In preferred embodiments the cantilevered rings do not have slots in the top or bottom of the cantilevered ring as this is where the energy from the cantilevered ring is generated. The cantilevered ring may also include a capacitative material such as rubber O-rings to further accelerate the speed of the microprojection array. FIGS. 10A to 10D show a number of different shapes, sizes and cutouts for cantilevered ring which may be utilized in the applicators of the present invention. The cantilevered rings may have a thickness of about 0.10 mm, or about 0.15 mm, or about 0.20 mm, or about 0.25 mm or about 0.30 mm, or about 0.35 mm or about 0.40 mm. The cantilevered rings may have a thickness of about 0.10 mm to about 0.40 mm or from about 0.10 to about 0.35 mm or from about 0.10 mm to about 0.30 mm, or from about 0.10 to about 0.25 mm or from about 0.10 mm to about 0.20 mm or from about 0.15 mm to about 0.40 mm or from about 0.15 to about 0.35 mm or from about 0.15 mm to about 0.30 mm, or from about 0.15 to about 0.25 mm or from about 0.15 mm to about 0.20 mm or from about 0.20 mm to about 0.40 mm or from about 0.20 to about 0.35 mm or from about 0.20 mm to about 0.30 mm, or from about 0.20 to about 0.25 mm. The thickness of the cantilevered ring may vary from point to point. The cantilevered rings may have a radius of curvature from about 40 to 110 mm.

In one embodiment of the applicators of the present invention the cantilevered ring(s) have a diameter of 30-40 mm with a height from the contact face to the top of the dome from 1.5 to 5.0 mm. The outer housing of the applicator may also be dome shaped. Preferably the shape of the outer housing and the device overall has a low profile.

The applicator housing may interface with a skin contact applicator base which is designed to contact the skin in such a way as to improve the interaction with the skin. The skin contact applicator base may be covered in whole or in part with a compliant material to control skin reactions that may otherwise disengage the patch or otherwise disrupt the engagement of the applicator on the skin. The skin contact applicator base, in whole or in part, may be collapsible.

Figure 5:
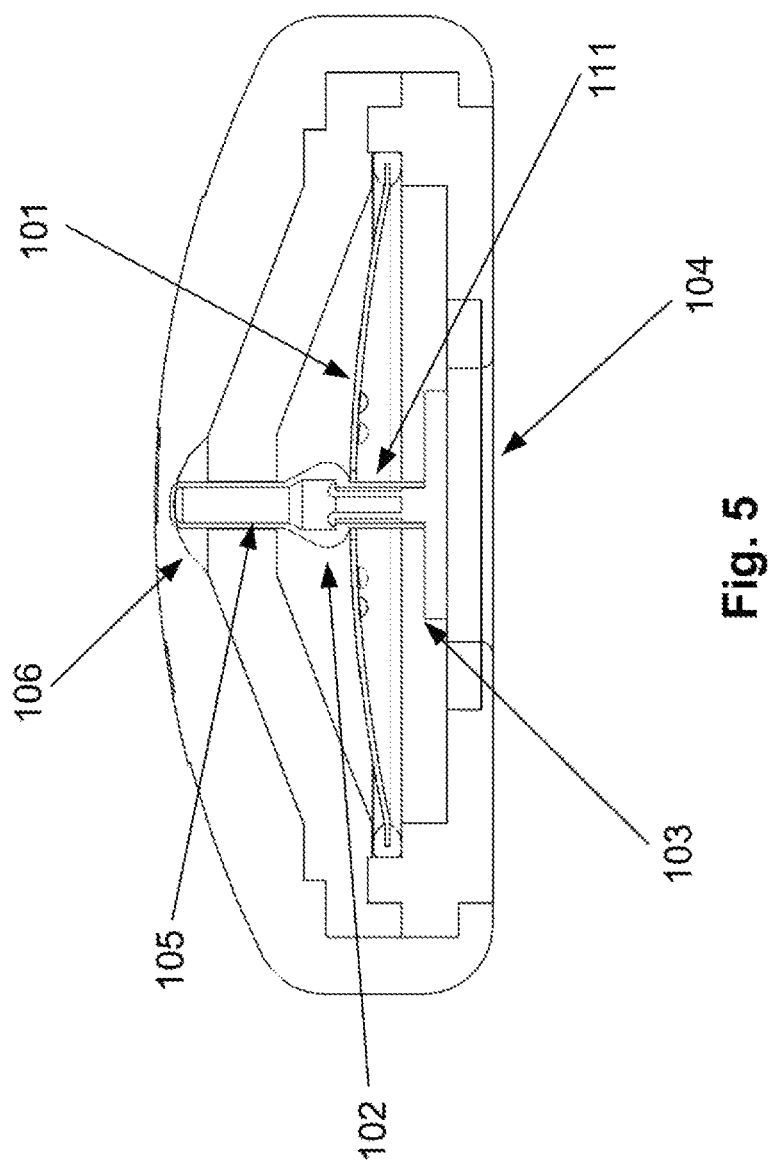
FIG. 5 is a cut-away view of one embodiment of the microprojection array applicator of the present invention prior to activation of the applicator.
Figure 6:
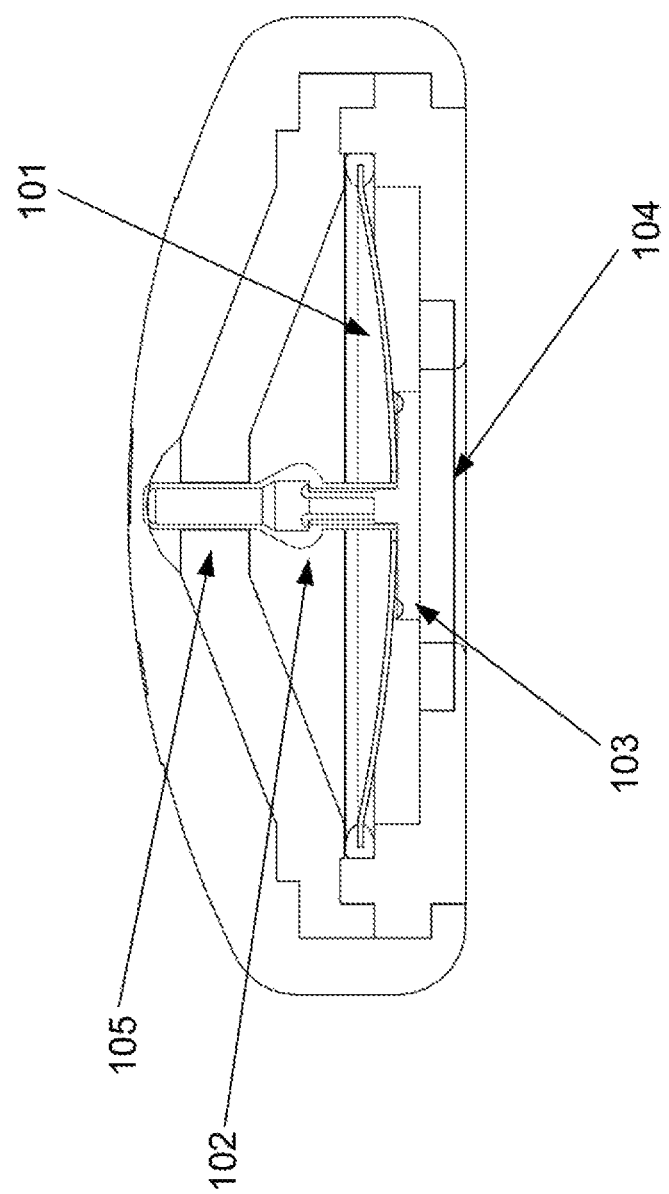
FIG. 6 is a cut-away view of one embodiment of the microprojection array applicator of the present invention after activation of the applicator. In this view the activated dome is beginning to contact the back of the microprojection array just prior to accelerating the array.
Figure 7:
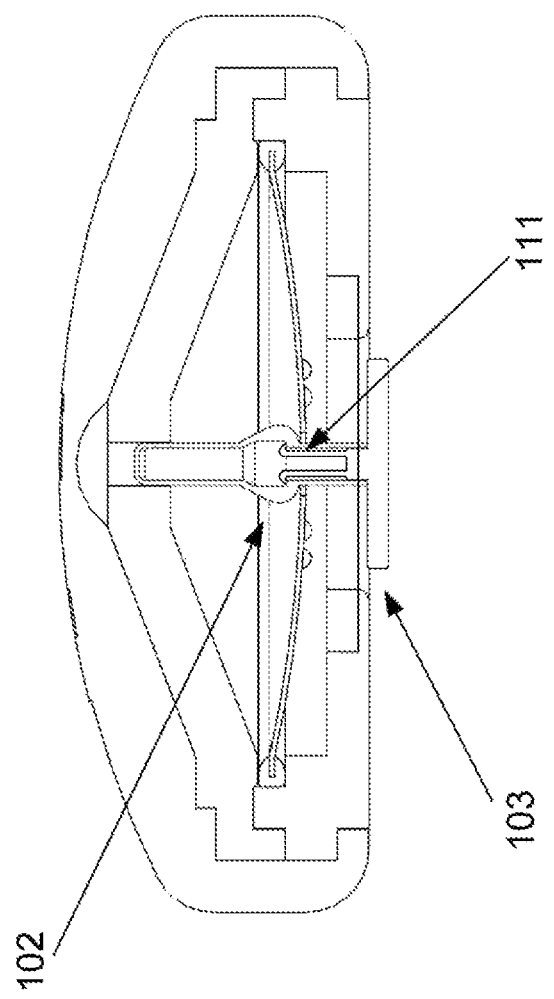
FIG. 7 is a cut-away view of one embodiment of the microprojection array applicator of the present invention showing how the cantilevered ring in combination with the stop mechanism prevents the microprojection array from freely flying away from the applicator.

In one embodiment the applicator is comprised of a housing containing a single cantilevered ring which translates the force to the microprojection array (FIG. 5). The applicator is comprised of a flexible applicator top (106), a patch guide (105) having a stop mechanism incorporated within (102), a cantilevered ring (dome) (101) optionally with capacitive material, a microprojection array which has a skin facing front side (103) and an applicator facing back side which has a protrusion (111) that interfaces with the patch guide (105), a skin contact membrane (104) and membrane support and skin contact applicator base (109, not seen in FIG. 5) and a foil lid or cover (108, also not seen in FIG. 5). The top of the patch guide is fitted in such a way within the device that it interacts with the flexible applicator top and the bottom of the patch guide protrudes through the dome and may provide guidance for the coated patch (microprojection array). In this embodiment of the applicator the microprojection array is made such that the back of the microprojection array (111) is connected to the patch guide (105) by merging them together in order for them to be able to be assembled through the dome. In an alternate embodiment the microprojection array/patch guide assembly is assembled through the dome by using a key hole in the dome. FIG. 5 shows the internal configuration of the applicator prior to actuation where the cantilevered ring is in the primed position. As can be seen in FIG. 5 in the primed position the microprojection array is housed inside the applicator housing where it is recessed therein and away from the skin. FIG. 6 shows the internal configuration of the applicator after actuation where the cantilevered ring has just been fired. The cantilevered ring is in the process of pushing against the back of the microprojection array (103). FIG. 7 shows a cross-sectional view of the applicator after the cantilevered ring has fired and has propelled the microprojection array towards the skin. In this position the microprojection array is no longer recessed within the applicator but has been propelled through the membrane and through the void in the applicator bottom and into the skin. The patch guide may also provide a stopping mechanism (102) such that the patch guide prevents the microprojection array from freely flying out of the applicator.

Figure 8:
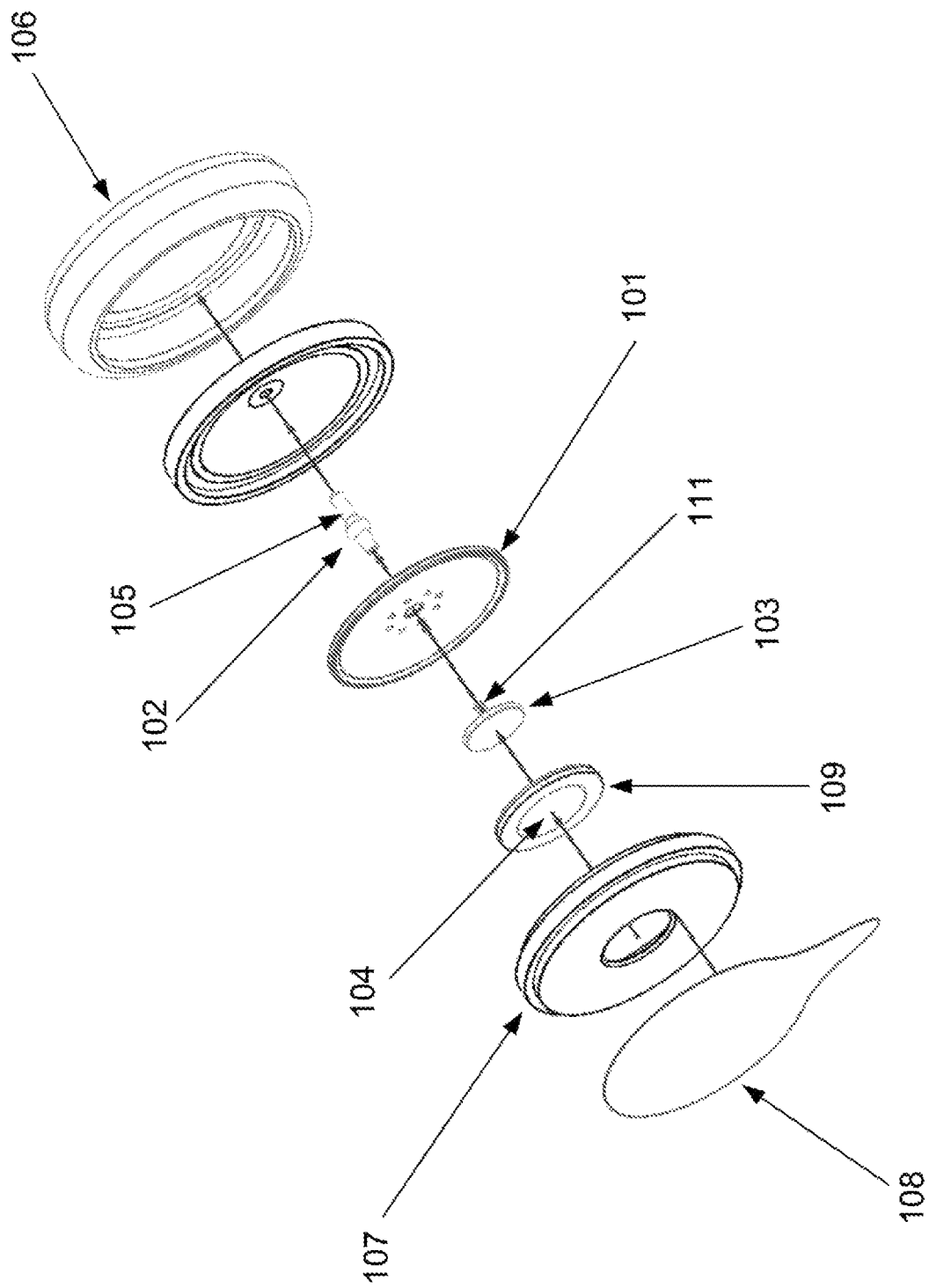
FIG. 8 is an exploded view of one embodiment of the microprojection array applicator of the present invention showing the various parts of the applicator.
Figure 10A:
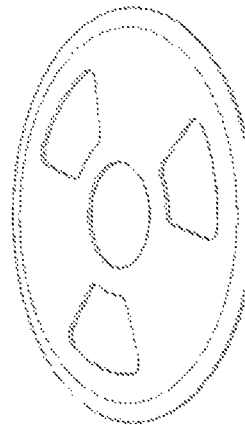
FIGS. 10A-10D are pictures of various dome designs without top or bottom cuts.
Figure 10B:
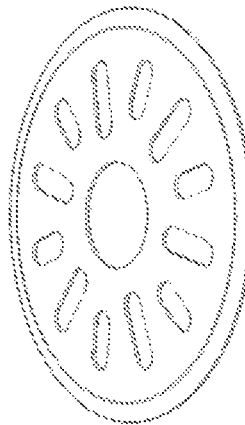
Figure 10C:
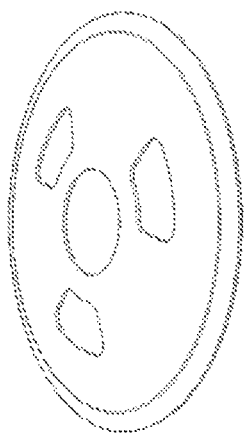
Figure 10D:
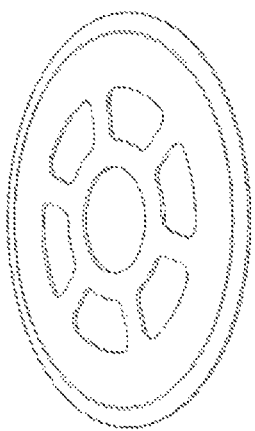
Figure 13A:
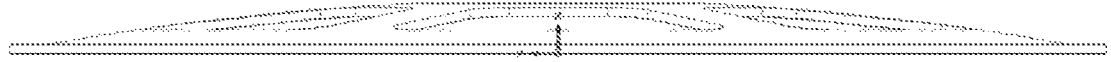
FIG. 13A is one embodiment of a cantilevered ring in an unloaded position; 13B is one embodiment of a cantilevered ring in a loaded or primed position; 13C is a top down view of one embodiment of a cantilevered ring showing the inner ring, outer ring, fold line and cantilevers.
Figure 13B:
Figure 13C:
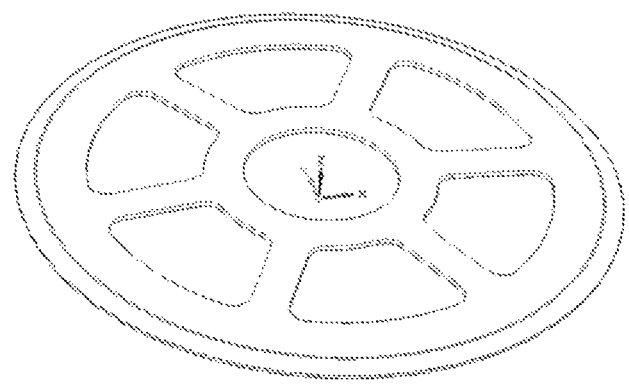

FIGS. 8 and 9 show exploded views of one embodiment of the microprojection array applicator of the present invention where the various parts of the applicator are labeled. The skin contact membrane is held by the membrane support (109) which attaches to the skin applicator base such that the skin contact membrane is positioned over the hole (110) in the skin contact applicator base (107). The skin contact applicator base is attached to the flexible applicator top to provide a sealed applicator. A foil cover may be placed over the skin applicator base to cover the membrane and coated patch prior to use. FIG. 13C shows the details of a cantilevered ring with a radial array of 6 cantilevers. This embodiment lowers the trigger force without lowering the cantilevered speed by much. The speed and force of the cantilevered rings may be for example 20 m/s @ ION trigger. The outer cantilevered ring is an energy storing element that provides the speed that moves the microprojection array forward upon buckling. The fold line localizes the stress and helps propagate the force to the full ring from a trigger point. Cantilevers enable the amplification of the movement generated by the buckling of the ring toward the patch, in a controlled symmetrical manner. This design is such that the cantilevers do not remove energy and as they do not need to buckle. Indeed, as can be seen in FIGS. 13A and B the curvature of the cantilever is the same in both loaded and unloaded states. In prior art designs the inner/center part of the dome must buckle as well so that the outer ring can buckle, thus requiring more force for a similar output speed. Moreover the array of cantilevers is stiff enough so that the force provided by the user is directly transmitted to the ring without deformation, therefore less force wasted. This can be demonstrated by plotting a graph of extension of deformation vs. load. A non-cantilevered dome will see an increase of the load with the deformation of the dome, until reaching a peak load, then the load will decrease as further deformation occurs and partial buckling happens until the dome snaps at a certain snap force (full buckling). In the case of the cantilevered ring, the peak load and the snap force are the same: the dome snaps close to the maximal load (see attached graph, axis are different). In embodiments of the applicator devices of the present invention the cantilevered rings (dome) deforms under load, snaps and start accelerating, reaches a peak speed and instantly starts decelerating. The microprojection array is placed at a position which is relatively fixed in relation to the ring, meaning the array moves when deforming the dome under load, keeping the same gap. But when the cantilevered rings snaps, the array virtually does not move relative to the rings and is at a distance from the dome that will enable the dome to reach its peak speed when coming into contact with the array. This is especially important for high density microprojection array. The microprojection array is not in contact with the cantilevered ring and is struck at a point where the dome achieves maximum velocity.

FIGS. 5-7 show a cut-away view of how the applicator is triggered and the results of actuating the device. FIG. 5 shows a cut-away view of the loaded device in which the device may be activated by pressing the top of the housing which then interacts with the patch guide (105) which can serve as a triggering mechanism and a stopping mechanism (102). FIG. 6 shows a cut-away view of the applicator after the device has been activated and at the point where the dome has snapped and impacts the back of the microprojection array which is then accelerated towards the membrane and then into the skin. FIG. 7 shows a cut-away of the applicator after the device has been triggered and the microprojection array has entered the skin. The patch guide (105) may also serve as a stopping device in that the shape of the guide is such that the guide will not completely pass through the hole in the dome. In FIG. 7 the patch guide is constructed such that between the proximal and distal end of the guide the diameter of the guide is large than the diameter of the hole in the dome such that the patch guide will not pass through the hole in the dome but rather be stopped by the dome. As described above this embodiment shows that the patch is made in two parts (the white patch guide (105) and the black microprojection array back (111)) that click together in order to be able to assemble them together through the dome.

In one embodiment the applicator is comprised of a housing containing a single dome which translates the force to the microprojection array. In another embodiment the applicator is comprised of a housing which contains two domes where the force is translated from one dome to the second dome (FIG. 14). In one embodiment multiple (two or more) cantilevered rings (domes) are stacked. Each of the rings occupies the same state (primed or fired). When the first dome (that closest to the top of the applicator) is triggered by the action of the user (directly, through a collapsible, deformable, pusher part etc.), the first cantilevered ring in turn triggers the next cantilevered ring(s). The domes do have not necessarily the same characteristics (force, speed, thickness, shape, design etc.). In a preferred embodiment the first dome is a low trigger force dome, which when triggered by the action of the user, in turn triggers the main or second dome. The benefit of this multiple dome system is having a trigger that is easy for the user to operate, and a high performance dome (speed) accelerating the patch. The first dome leverages the potential higher actuation force of the main dome. The domes can be in close contact or at optimized distance from each other, such that one dome contacts the next dome at the first dome's peak speed or force. The optimized spacing of the domes may be achieved by in a variety of ways such as different thickness of the domes, special features on the dome, housing of the domes in the applicator with a gap between them in some cases mediated by a spacer. Another preferred embodiment is a stack of several domes where the speed of the final dome is higher than a single dome due to the combined acceleration of the previous domes.

Figure 14A:
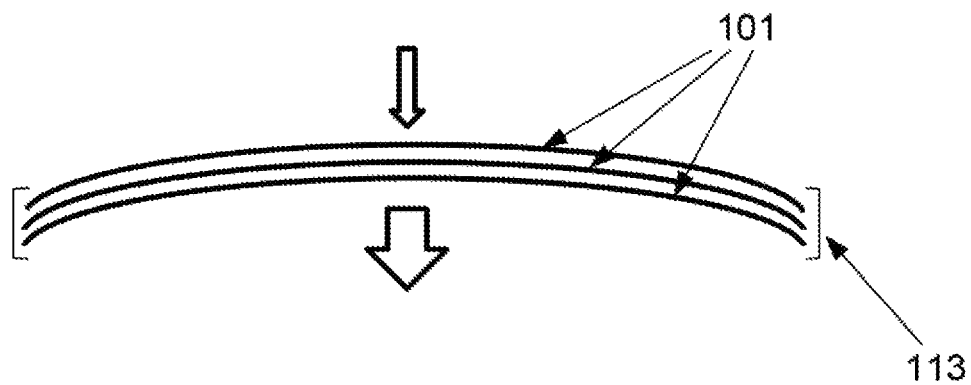
FIG. 14A is a schematic drawing of a side view of one embodiment of the microprojection array applicator in which multiple domes (cantilevered rings) which are directly stacked upon one another are used in the applicator.
Figure 14B:
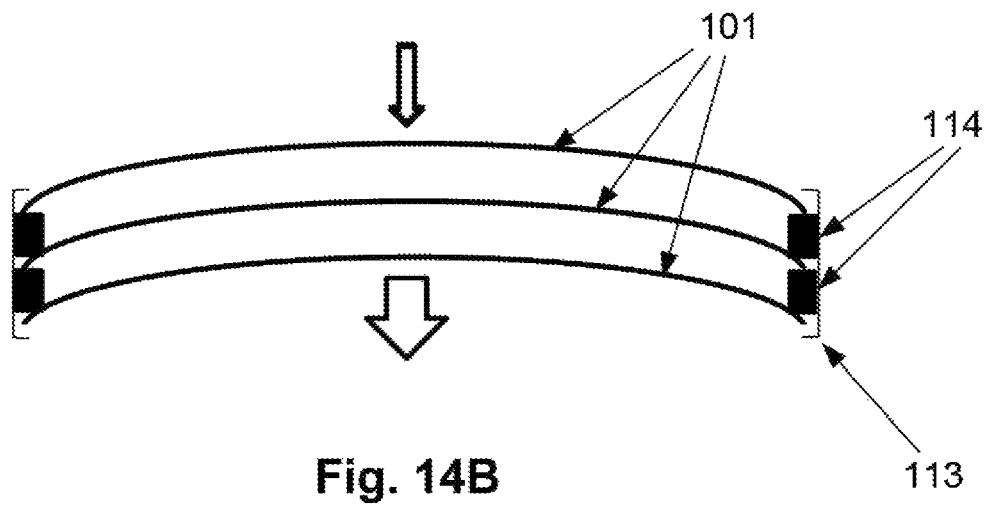
FIG. 14B is a schematic drawing of a side view of one embodiment of the microprojection array applicator in which multiple domes (cantilevered rings) which are stacked upon one another at a fixed gap are used in the applicator.

In the example of FIG. 14A, three domes (101) are directly stacked on each other, and supported by an applicator dome stack housing (113). The upper dome (101) is the first to be triggered, then triggers subsequent domes (101) in a cascade. In the example of FIG. 14B, three domes (101) are stacked with a fixed gap to each other. The domes (101) are supported by an applicator dome stack housing (113), but in this case adjacent domes (101) are spaced apart by respective spacers (114). Once again, the upper dome (101) is the first to be triggered, then triggers subsequent domes (101) in a cascade.

Figure 15:
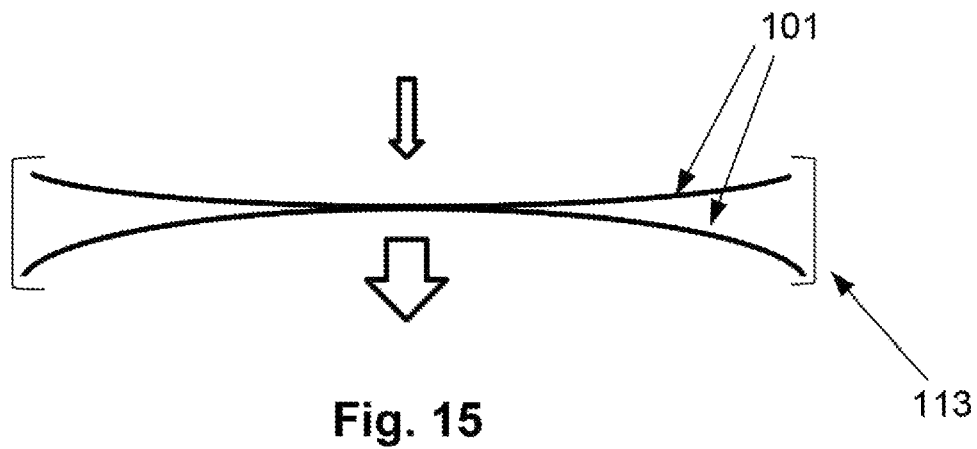
FIG. 15 is a schematic drawing of a side view of one embodiment of the microprojection array applicator in which two domes (cantilevered rings) are used in the applicator where one ring is inverted relative to the other ring.

Another embodiment of the microprojection array applicator is shown in FIG. 15, where at least one of the domes (101) is inverted with respect to at least one of the other domes. In one embodiment there are two domes where the second dome (bi-stable dome) accelerates the patch. The first "dome" can be either primed or fired or even be a generic spring (compression, washer, waved etc.). The purpose of this first dome is to provide a continuous load on the main dome in order to decrease the load required by the user to trigger the main dome. A preferred embodiment is where the first dome provides enough load so that the remaining force to trigger the main dome is provided by the user. The load applied by the user [x % of the trigger force F] complements the load [100% of F-x] provided by the compression of the bi-stable dome. The applicator dome stack hosing keeps the two domes in compression resulting in the bi-stable dome being under a partial load. This embodiment is useful for high speed main domes that have a high trigger force as a drawback. In this embodiment the applicator housing may sustain the load of bringing these two opposite domes together, whereas in the stacked domes embodiments no load is applied to the housing of the applicator. These embodiments have the benefit of having the pre-load continuous with the deformation of the main dome by the user. If the applicator supplied a load on the main dome by itself, as soon as the user pushed the main dome, the dome would disconnect from the constraint of the applicator and the full counter force would push back to the user.

The two domes may either be in contact with one another or have some space between. The housing may have a concave shape and the domes may have a concave shape in which the radius of curvature is about 80 mm and a microprojection array. The outer housing may be made of plastic or a metallic material such as steel or aluminum or a fibrous paper based material or a laminate including any of these materials and may have a collapsible section which acts as a trigger to activate the dome(s). The applicator may further include a thin membrane covering the opening through which the microprojection array must pass. The applicator may also include a cover or label that can be peeled away from the membrane for further protection of the microprojection array until it is used.

The applicators of the present invention may deliver the microprojection arrays to the skin in at least two ways. In one embodiment the microprojection array may be attached to the device in such a way that the microprojection array remains attached to the device after the device is activated and the microprojection array enters the skin. In this embodiment the microprojection array may be fixed in the device by manufacturing a detail in the dome such that the microprojection array may be snap fit into the detail. In another embodiment the back of the microprojection array has a detail that allows it to engage with the device. For example this could be in the form of a spigot, magnet or other shape that mechanically allows the back of the microprojection array to connect to the firing mechanism. This detail, be it a bore or a spigot is further used as a guide to ensure that the patch during flight tracks perpendicular to the device and cannot strike the skin at an inappropriate angle. The detail on the back of the microprojection array also tethers the patch to the device, in this way the patch is free to "fly" forward and strike the skin but is still attached to the device, this renders the device safe as the patch cannot be shot out of the device and allows the patch and the applicator to be removed from the skin as a single unit. The detail on the back of the patch allows the patch to be fired forward onto the skin, this forward movement is restricted in that the patch is still connected to the applicator and cannot come all the way out. In this way when the applicator is removed from the skin the patch comes away with it. The detail on the back can also allow the patch to be engaged in the device at various positions. For example there may be a coating position, in this position the spigot on the back of the patch is connected to the applicator and when engaged it sits proud of the front face. This means that the device and patch can be coated with vaccine as one unit. Once coated the patch is then pushed back into the device to its "loaded" position.

Alternatively the microprojection array may be fixed to the device by adhering the array to the dome by a flexible adhesive such as silicone. An adhesive, such as silicone, may be cast around the array perimeter placed in a dome such that it forms a wall that contains the array. When the dome inverts the walls open out allowing the patch to be ejected. This opening wall that encases the patch may also be designed into the dome. In this embodiment the applicator may also be used to remove the microprojection array from the skin after activation and penetration of the microprojection array into the skin. In one embodiment, the microprojection array may be removed by the applicator as a result of the dome to which the array is attached snaps back to its original position. In an alternate embodiment the microprojection array may be removed from the skin in a controlled manner using a levering mechanism that can be manipulated to insure that the removal of the device is not painful to the patient.

The microprojection array may be propelled from the device after the device is activated such that the microprojection array transits a distance between the applicator device and the target skin and then penetrates the skin. In essence, the microprojection array may be propelled across some distance and then penetrate the target skin. In one embodiment of the applicator where the microprojection array is discharged from the device, the microprojection array could be tethered to a mechanism that protrudes through the cantilevered ring (dome) such that when the dome is activated the mechanism releases the microprojection array with sufficient force to propel the array into the skin. For example, the microprojection array could be fixed to a guide shaft (patch guide) that fits through a center hole in the dome. The patch guide enables guided travel of the microprojection array to ensure that the microprojection array contacts the skin in a flat manner, so that the microprojection array and the skin meet flush. In this embodiment the microprojection array and the cantilevered ring are disconnected such that the large mass of the ring is not attached to the array. This should permit a high speed, low mass, pain free delivery of the microprojection array to the skin. In another embodiment the microprojection array may be attached to a low mass tether. In this embodiment the microprojection array is either not in direct contact with the dome or the only contact between the cantilevered ring and the microprojection array is when the ring impacts the array sending the array toward the skin. In these cases the microprojection array can be struck at the point where the dome achieves maximum velocity and the mass of the cantilevered ring does not impact the skin of the patient. In preferred embodiments of the applicator device of the present invention the microprojection array is either propelled without attachment to the device or attached to the device via a low mass connector such as a tether.

Prior art applications of microprojection arrays utilize 'high-force, low velocity' applicators. Such applicators may lead to bruising of patients or unwanted cellular damage during the application of the microprojection arrays. Prior art applicators were often devices that were designed to provide a uniform and repeatable force behind a needle or array of needles that could usually be inserted into the skin by means of a hand applied force. For high density arrays any amount of force applied manually will not overcome the elasticity of the skin due to the "bed of nails" effect. The applicators of the present invention utilize a 'low-force, higher velocity' applicator which may use a "flying" microprojection array in which the microprojection array is discharged from the device with sufficient force to propel the array through space and into the skin. Peak stresses are associated with the penetration of projections, without the follow-through, and the higher velocity achieves the change of behaviour of the skin from elastic to plastic. The use of low force, high velocity approach to penetration of the skin by the microprojection array provides advantages such as: achieving equivalent penetration in the skin, but with about only 1/10th the Kinetic Energy; improved patient acceptability/tolerability of the penetration of the skin by the microprojection array and significantly less breakage of projections (up to about 1/10000 reduction of breakage) and patch base. The use of low force, high velocity application of the microprojection array to the skin also provides consistent penetration of the patch from site to site, because the mechanics of penetration are not heavily reliant on variations of the subcutaneous tissue (which does vary significantly within and individual and between people in populations. The direct correlation of kinetic energy with penetration may be utilized to design an applicator and microarray projections that provides maximal efficiency in delivering material to the patient while reducing discomfort to the patient.

It should be appreciated that the use of a cantilevered ring (dome) in the present invention also provides significant advantages to conventional microprojection array applicators which involve piston-like propulsion of the microprojection array, usually using a coil spring or the like. Unlike the piston-like applicators, in the present invention the microprojections can penetrate the skin without bouncing off the skin and without the discomfort and bruising of prior devices. The cantilevered rings/domes are superior to springs in that they can allow the microprojection array to achieve higher velocities as discussed above, and in practice this is achieved with a reduced distance of movement, which can result in a more compact device. In this regard, it is noted that piston-like applicators with coil spring mechanisms typically require the device to extend a significant distance from the skin surface to accommodate the spring and piston movement. In contrast, the use of cantilevered rings/domes in the present invention allows a significant reduction in the size of the device measured from the skin surface.

In one embodiment the microprojection array is applied by removing the label and placing the applicator membrane on the surface of the skin. The collapsible section of the housing is depressed activating the first dome. The first dome strikes the second dome which releases the microprojection array. The microprojection array pierces the membrane and penetrates the skin. The applicator can be removed after a period of time and then discarded.

The speed of the microprojection array as it is projected into the skin depends at least in part upon the density of the projections in the microarray and the area of the array. The range of speeds for the microprojection array entering the skin may be from about 10 m/s to about 50 m/s or from about 10 m/s to about 40 m/s or from about 10 m/s to about 30 m/s or from about 10 m/s to about 25 m/s or from about 10 m/s to about 20 m/s or from about 20 m/s to about 50 m/s or from about 20 m/s to about 40 m/s or from about 20 m/s to about 30 m/s or from about 25 m/s to about 50 m/s or from about 25 m/s to about 40 m/s or from about 25 m/s to about 30 m/s. In preferred embodiments of the microprojection applicators of the present invention the speed of the microprojection array is at least 15 m/s or at least 20 m/s or at least 25 m/s or at least 30 m/s.

The microprojection arrays that the applicator of the present invention projects into the skin may have a variety of shapes and sizes. The microprojection array may be square, circular, rectangular or irregular depending on its use. The microprojection arrays can be varied in size depending on its use. The area of the patch will have an impact on the ability to penetrate the subject, but this must be balanced by the need to induce cell damage over a sufficiently large area to induce a response. Consequently the patch typically has an area of between 0.5×0.5 mm and 20×20 mm, between 0.5×0.5 mm and 15×15 mm and more typically between 1×1 mm and 10×10 mm.

In one embodiment the microprojection array is 10×10 mm. The microprojection arrays may have a density of projections of between 1,000 to 20,000 per $cm^2$ or from 1,000 to 15,000 per $cm^2$, or from 1,000 to 10,000 per $cm^2$ for from 1,000 to 5,000 per $cm^2$, or from 2,500 to 20,000 per $cm^2$ or from 2,500 to 15,000 per $cm^2$ or from 2,500 to 10,000 per $cm^2$ or from 2,500 to 7,500 per $cm^2$ or from 2,500 to 5,000 per $cm^2$ or from 5,000 to 20,000 per $cm^2$ or from 5,000 to 15,000 per $cm^2$ or from 5,000 to 10,000 per $cm^2$ or from 5,000 to 9,000 per $cm^2$ or from 5,000 to 8,000 per $cm^2$ or from 5,000 to 7,000 per $cm^2$ or from 5,000 to 6,000 per $cm^2$. The applicators of the present invention are often utilized to project high density microprojection arrays into the skin. Such high density arrays are microprojection arrays of sufficient size and density such that forces that can be applied manually will be insufficient to overcome the elasticity of the skin. The projections are typically separated by between 10 μm and 200 μm, between 30 μm and 150 μm, between 50 μm and 120 μm and more typically between 70 μm and 100 μm, leading to patches having between 10 and 1000 projections per $mm^2$ and more typically between 100 and 3000 projections per $mm^2$, and in one specific example approximately 20,000 per $cm^2$.

The length of the projections may be from 100 μm to 700 μm or from 100 μm to 600 μm or from 100 μm to 500 μm or from 100 μm to 400 μm or from 100 μm to 300 μm or from 100 μm to 250 μm or from 100 μm to 200 μm or from 150 μm to 700 μm or from 150 μm to 600 μm or from 150 μm to 500 μm or from 150 μm to 400 μm or from 150 μm to 300 μm or from 150 μm to 250 μm or from 150 μm to 200 μm or from 200 μm to 700 μm or from 200 μm to 600 μm or from 200 μm to 500 μm or from 200 μm to 400 μm or from 200 μm to 300 μm or from 200 μm to 250 μm or from 225 μm to 700 μm or from 225 μm to 600 μm or from 225 μm to 500 μm or from 225 μm to 400 μm or from 225 μm to 300 μm or from 225 μm to 250 μm or from 250 μm to 700 μm or from 250 μm to 600 μm or from 250 μm to 500 μm or from 250 μm to 400 μm or from 250 μm to 300 μm. The projections may have a step shoulder between the cone and pillar of the projection. The microprojection array may be made of any suitable materials including but not limited to silicon, polymers, and plastic. In silicon embodiments the base thickness is about 60 um or silicon with a thin (1 mm) polymer backing. The overall mass of some embodiments of the microprojection array is about 0.3 gm. The microprojection array may have bevelled edges to reduce peak stresses on the edge of the array. Quartered dicing to reduce the stress load on the patch and mitigate patch breakage. Polymer embodiments may have reduced mass. The microprojection array may also have an overall weakly convex shape of the patch to improve the mechanical engagement with skin and mitigate the effect of high speed rippling application: a 'high velocity/low mass' system. The microprojection array may have a mass of less than 1 gram, or less than 0.9 grams or less than 0.8 grams or less than 0.7 grams, or less than 0.6 grams or less than 0.5 grams or less than 0.6 grams, or less than 0.5 grams or less than 0.4 grams or less than 0.3 grams or less than 0.2 grams or less than 0.1 grams or less than 0.05 grams. The microprojection array may have a mass of about 0.05 grams to about 2 grams, or from about 0.05 grams to about 1.5 grams or from about 0.05 grams to about 1.0 grams or from about 0.05 grams to about 0.9 grams, or from about 0.05 grams to about 0.8 grams or from about 0.05 grams to about 0.7 grams, or from about 0.05 grams to about 0.6 grams or from about 0.05 grams to about 0.5 grams or from about 0.05 grams to about 0.4 grams, or from about 0.05 grams to about 0.3 grams or from about 0.05 grams to about 0.2 grams, or from about 0.05 grams to about 0.1 grams or from about 0.1 grams to about 1.0 grams or from about 0.1 grams to about 0.9 grams, or from about 0.1 grams to about 0.8 grams or from about 0.1 grams to about 0.7 grams, or from about 0.1 grams to about 0.6 grams or from about 0.1 grams to about 0.5 grams or from about 0.1 grams to about 0.4 grams, or from about 0.1 grams to about 0.3 grams or from about 0.1 grams to about 0.2 grams. In one embodiment of the applicator/microprojection system the mass of the array is about 0.3 grams, the array is projected at a velocity of about 20-26 m/s by the applicator. In some embodiments there is no pre-compression of the skin. A small recoil allows the applicator to not be in contact with the skin when the skin impact waves move laterally. This may have the effect of reducing the effect of rippling.

The microprojection arrays may be coated by various materials intended to have a prophylactic or preventative effect. The various materials with which the microprojections may be coated are described in US Patent Publication No. 2014/0257188 hereby incorporated by reference. At least a portion of the projections may be coated. Accordingly, one way of providing material for delivery to the biological subject is by providing the material within the coating. For example, the coating may include a vaccine for providing an immunological response within the subject. However, the projections may also be provided in an uncoated state to provide physical stimulus to tissues within the biological subject without actually delivering material. This can result in bystander interactions in neighboring cells, which may provide a physical adjuvant effect, irrespective of whether materials are delivered.

The coating may be provided in liquid or non-liquid forms, and may further include ingredients other than the material to be delivered, such as an adjuvant. Suitable coating formulations for use with projections patches and methods of applying such coatings to the projections are known.

Although any type of coating may be used, particularly advantageous embodiments of the patch are provided with at least a portion of the projections coated with a non-liquid coating. In this regard, the term "non-liquid" coating will be understood to include a coating that is applied in a liquid form and allowed to dry or otherwise solidify to thereby form a non-liquid coating. In some embodiments, more than one non-liquid coatings can be applied to the same projections. For instance, different coatings may be applied in layers to provide different materials for delivery to the tissues within the subject at different times, as the layers dissolve in sequence. A first coating may be applied to modify surface properties of the projection and improve the ability of the second coating to coat the projection in a desirable manner. Multiple layers of the same coating formulation may be used with drying between each layer to allow a progressive build up coating to achieve an increased thickness and thus modify the effective cross section even further.

The present invention further relates to microprojection applicators in which a membrane is introduced between the microprojection array and the skin surface to which the array is applied. The membrane flattens the skin to which the microprojection array is applied and absorbs the initial impact from the microprojection applicator (FIG. 6-7). The use of a membrane results in an even surface for application regardless of skin condition or thickness and provides even penetration of the microprojections across the skin surface. Microprojection application through a membrane has distinct advantages over application of a microprojection array directly into the skin. It allows the skin to be smoothed flat creating a consistent and uniform application surface. As can be seen in Example 1, the use of the membrane greatly improves the narrowness of the ranges of penetration into the skin. The use of a membrane over the microprojection array allows a device design whereby the microprojection array can be kept in a sterile environment until the membrane is pierced at the time of application. The membrane also allows the patch to be removed from the skin with the applicator and provides confirmation of the application of the microprojection array via the penetration pattern visible on the membrane surface. The membrane also reduces the need for external packaging to maintain sterility thereby reducing packaging waste. Preferably the membrane is non-permeable. The membrane may be made of but is not limited to polymer films, organic and organic fiber films or laminates. Preferably the membrane is from about 2 to about 20 μm or from about 5 to 20 μm or from about 10 to about 20 μm or from about 5 to 10 μm in thickness. The membrane may also include a material either coated on its surface or impregnated into the membrane. The material may have a therapeutic or prophylactic effect. In one embodiment the membrane may contain a therapeutic agent to assist in wound healing or agents such as anti-inflammatory, analgesic or antibiotics.

The membrane and the bottom of the applicator may also be covered in part or in full by a label or covering which serves to protect and keep sterile the membrane and the microprojection array. The label may be in the form of a foil seal that can be removed just prior to the use of the microprojection array applicator. In embodiments where a membrane is not used the label may cover the microprojection array.

A desiccant film may be included in the microprojection array applicator to maintain the internal environment and water content of the coating. One method of incorporating a desiccant into the applicator is by incorporating the desiccant into the membrane which may be layered under the foil seal or internal to the device housing. The desiccant may be incorporated into the housing or any moulded materials in the device.

The devices of the present invention may be multiple use devices or single use devices or disposable devices. Furthermore, the applicators of the present invention can be sterile and permit the packaging of the device in a sealed container to prevent contamination.

The devices of the present invention, once used, can be disposed of in a cost effective and environmentally effective way. There is emphasis these days on full life cycle management products not only for how a product is used and packaged but also rendered safe and disposed of at the end of its life. Also from an economic point of view the total cost of a product includes disposal the impact on the environment. Incineration of medical waste is no longer the preferred method of disposal, it is expensive and hard to meet the stringent EU guidelines for pollutants. A preferred approach is to disinfect the waste through the use of steam or chemical means and then separate into component parts for recycling or burial as non-contaminated landfill. The devices of the present invention reduce contaminated waste incineration by using materials that emit a minimum of toxins upon incineration, reduce volume of packaging and device. The devices of the present invention reduce deep burial waste by reducing the volume of packaging and device. The devices of the present invention reduce chemical disinfection and burning or burial by reducing the volume of packaging and device, design to allow the ingress of cleaning solution post use. The devices of the present invention permit the use of steam disinfection and separation of parts into recycled waste by reducing the volume of packaging and device, design to allow the ingress of steam post use, design to use materials that can be easily recycled. The devices of the present invention use biodegradable materials (polymers) in its manufacture. The devices of the present invention include in the design a feature that allows the contaminated parts to be easily removed from the device after use (such as the patch, membrane and bottom contact surface). In this manner the contaminated waste can be reduced to its absolute minimum.

In some embodiments of the microprojection array applicators and methods of applying the microprojection arrays to the skin the parameters for delivering the microprojection array may be: application momentum 6-22 g·m·s-1, application momentum per projection 1-4 mg·m·s-1, application energy 65-165 mJ; application energy per projection 10-40 μJ; dome mass 0.5-2 g; patch velocity 15-24 m·s-1. In some embodiments of the microprojection array applicators and methods of applying the microprojection arrays to the skin the parameters for the patch may include patch mass 265-1400 mg; patch number of projections 5,000-21,000; tip radius; patch size 4×4 mm to 11×11 mm (round diameter of 10 mm); length of projection 100-300 μm; base width 20-50 μm; projection spacing 70-185 μm; projection density 10-200 projections/mm$^2$.

Illustrative stimuli or material that can be delivered with the microprojection array delivered by the applicator device and methods of the present invention include any or more of: small chemical or biochemical compounds including drugs, metabolites, amino acids, sugars, lipids, saponins, and hormones; macromolecules such as complex carbohydrates, phospholipids, peptides, polypeptides, peptidomimetics, and nucleic acids; or other organic (carbon containing) or inorganic molecules; and particulate matter including whole cells, bacteria, viruses, virus-like particles, cell membranes, dendrimers and liposomes.

In specific embodiments, the stimuli or material are selected from antigens including endogenous antigens produced by a host that is the subject of the stimulus or material delivery or exogenous antigens that are foreign to that host. The antigens may be in the form of soluble peptides or polypeptides or polynucleotides from which an expression product (e.g., protein or RNA) is producible. In some embodiments antigens are selected from pathogenic organisms which include, but are not limited to, viruses, bacteria, fungi parasites, algae and protozoa and amoebae. Illustrative viruses include viruses responsible for diseases including, but not limited to, measles, mumps, rubella, poliomyelitis, hepatitis A, B (e.g., GenBank Accession No. E02707), and C (e.g., GenBank Accession No. E06890), as well as other hepatitis viruses, influenza, adenovirus (e.g., types 4 and 7), rabies (e.g., GenBank Accession No. M34678), yellow fever, Epstein-Barr virus and other herpesviruses such as papillomavirus, Ebola virus, influenza virus, Japanese encephalitis (e.g., GenBank Accession No. E07883), dengue (e.g., GenBank Accession No. M24444), hantavirus, Sendai virus, respiratory syncytial virus, othromyxoviruses, vesicular stomatitis virus, visna virus, cytomegalovirus and human immunodeficiency virus (HW) (e.g., GenBank Accession No. U18552). Any suitable antigens derived from such viruses are useful in the practice of the present invention. For example, illustrative retroviral antigens derived from HIV include, but are not limited to, antigens such as gene products of the gag, pol, and env genes, the Nef protein, reverse transcriptase, and other HIV components. Illustrative examples of hepatitis viral antigens include, but are not limited to, antigens such as the S, M, and L proteins of hepatitis B virus, the pre-S antigen of hepatitis B virus, and other hepatitis, e.g., hepatitis A, B, and C, viral components such as hepatitis C viral RNA. Illustrative examples of influenza viral antigens include; but are not limited to, antigens such as hemagglutinin and neurarninidase and other influenza viral components. Illustrative examples of measles viral antigens include, but are not limited to, antigens such as the measles virus fusion protein and other measles virus components. Illustrative examples of rubella viral antigens include, but are not limited to, antigens such as proteins E1 and E2 and other rubella virus components; rotaviral antigens such as VP7sc and other rotaviral components. Illustrative examples of cytomegaloviral antigens include, but are not limited to, antigens such as envelope glycoprotein B and other cytomegaloviral antigen components. Non-limiting examples of respiratory syncytial viral antigens include antigens such as the RSV fusion protein, the M2 protein and other respiratory syncytial viral antigen components. Illustrative examples of herpes simplex viral antigens include, but are not limited to, antigens such as immediate early proteins, glycoprotein D, and other herpes simplex viral antigen components. Non-limiting examples of varicella zoster viral antigens include antigens such as 9PI, gpII, and other varicella zoster viral antigen components. Non-limiting examples of Japanese encephalitis viral antigens include antigens such as proteins E, M-E, M-E-NS 1, NS 1, NS 1-NS2A, 80% E, and other Japanese encephalitis viral antigen components. Representative examples of rabies viral antigens include, but are not limited to, antigens such as rabies glycoprotein, rabies nucleoprotein and other rabies viral antigen components. Illustrative examples of papillomavirus antigens include, but are not limited to, the L1 and L2 capsid proteins as well as the E6/E7 antigens associated with cervical cancers, See Fundamental Virology, Second Edition, eds. Fields, B. N. and Knipe, D. M., 1991, Raven Press, New York, for additional examples of viral antigens.

At least a portion of the microprojections may be coated. Accordingly, one way of providing material for delivery to the biological subject is by providing the material within the coating. For example, the coating may include a vaccine for providing an immunological response within the subject. However, the microprojections may also be provided in an uncoated state to provide physical stimulus to tissues within the biological subject without actually delivering material. This can result in bystander interactions in neighbouring cells, which may provide a physical adjuvant effect, irrespective of whether materials are delivered, as will be described in further detail below. The coating may be provided in liquid or non-liquid forms, and may further include ingredients other than the material to be delivered, such as an adjuvant. Suitable coating formulations for use with projections patches and methods of applying such coatings to the projections are known, as described, for example, in WO/2010/042996 and WO/2009/079712. Although any type of coating may be used, particularly advantageous embodiments of the patch are provided with at least a portion of the projections coated with a non-liquid coating. In this regard, the term "non-liquid" coating will be understood to include a coating that is applied in a liquid form and allowed to dry or otherwise solidify to thereby form a non-liquid coating.

In some embodiments of the microprojection array applicators, the device may have a housing having a flexible section and a base defining an opening that in use is provided in contact with the skin surface; a patch guide movably mounted within the housing, wherein the patch guide supports a microprojection array in use; and a biasing member supported by the housing and movable from a first position to a second position upon deformation of the flexible section, wherein the biasing member urges the microprojection array into engagement with a skin surface through the opening.

Figure 11A:
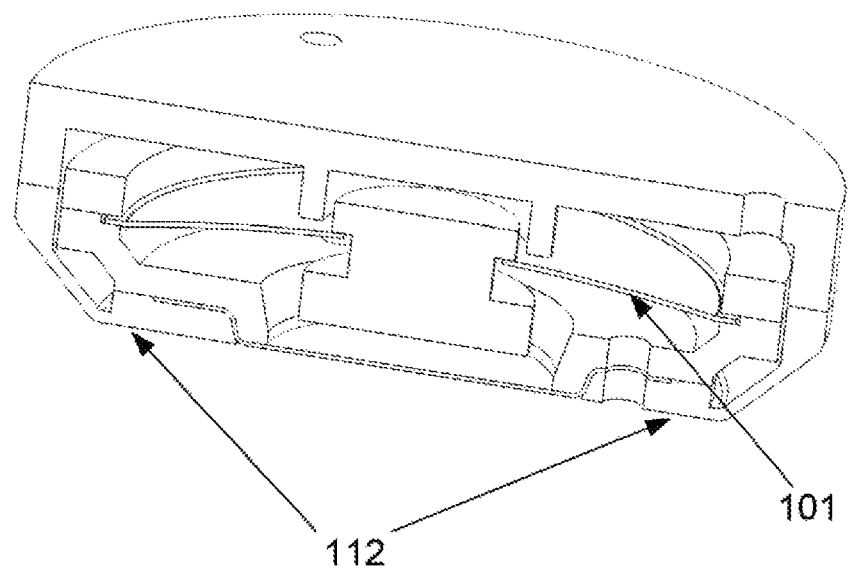
FIG. 11A is a cut away view of one embodiment of the microprojection array applicator in which the bottom portion of the applicator is deformable and is shown prior to deformation.
Figure 11B:
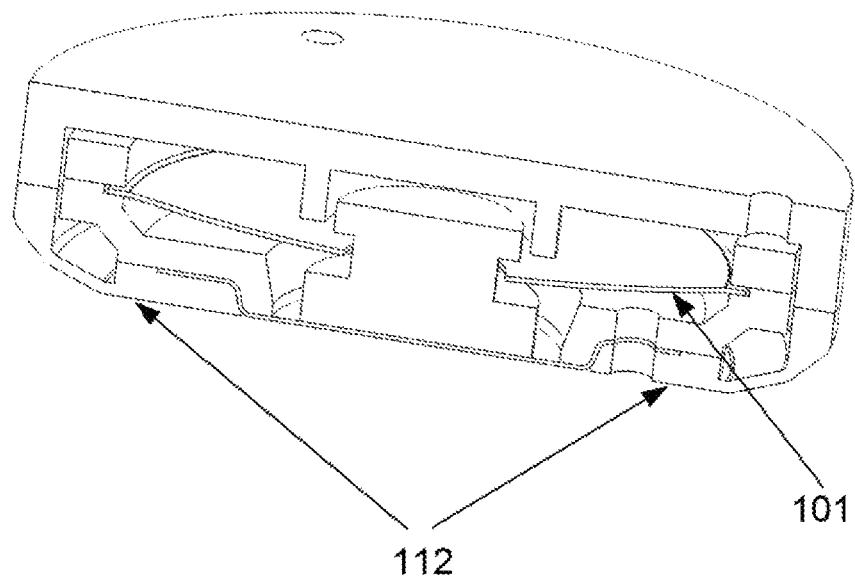
FIG. 11B is a cut away view of one embodiment of the microprojection array applicator in which the bottom portion of the applicator is deformable and is shown after deformation.

The biasing member may be in the form of a cantilevered ring or dome as discussed above. In some examples, the deformation of the flexible section causes the biasing member to be urged from the first position to the second position by a part of the patch guide, as shown in FIG. 5, for example. Alternatively, the deformation of the flexible section causes the biasing member to be urged from the first position to the second position by a part of the housing, as shown in FIG. 11, for example.

In other embodiments of the microprojection array applicators, the device may have a housing having a base defining an opening that in use is provided in contact with the skin surface; a patch guide movably mounted within the housing, wherein the patch guide supports a microprojection array in use; a trigger; a skin contact membrane provided in the opening; and a biasing member supported by the housing and movable from a first position to a second position upon activation of the trigger, wherein the biasing member urges the microprojection array through the skin contact membrane and into engagement with a skin surface through the opening.

As per the previously mentioned embodiments, the biasing member may be in the form of a cantilevered ring or dome as discussed above. The trigger may be provided by a part of the patch guide as shown in FIG. 5.

It will be appreciated that the above embodiments utilising a flexible section and a skin contact membrane may be combined. In one example, the deformation of the flexible section may be used to activate the trigger to thereby cause the biasing member to urge the microprojection array through the skin contact membrane and into engagement with a skin surface through the opening. In examples where the trigger is provided by a part of the patch guide, another part of the patch guide may provide the above mentioned functionality of urging the biasing member from the first position to the second position.

Within this disclosure, any indication that a feature is optional is intended provide adequate support (e.g., under 35 U.S.C. 112 or Art. 83 and 84 of EPC) for claims that include closed or exclusive or negative language with reference to the optional feature. Exclusive language specifically excludes the particular recited feature from including any additional subject matter. For example, if it is indicated that A can be drug X, such language is intended to provide support for a claim that explicitly specifies that A consists of X alone, or that A does not include any other drugs besides X. "Negative" language explicitly excludes the optional feature itself from the scope of the claims. For example, if it is indicated that element A can include X, such language is intended to provide support for a claim that explicitly specifies that A does not include X. Non-limiting examples of exclusive or negative terms include "only," "solely," "consisting of," "consisting essentially of," "alone," "without", "in the absence of (e.g., other items of the same type, structure and/or function)" "excluding," "not including", "not", "cannot," or any combination and/or variation of such language.

Similarly, referents such as "a," "an," "said," or "the," are intended to support both single and/or plural occurrences unless the context indicates otherwise. For example "a dog" is intended to include support for one dog, no more than one dog, at least one dog, a plurality of dogs, etc. Non-limiting examples of qualifying terms that indicate singularity include "a single", "one," "alone", "only one," "not more than one", etc. Non-limiting examples of qualifying terms that indicate (potential or actual) plurality include "at least one," "one or more," "more than one," "two or more," "a multiplicity," "a plurality," "any combination of," "any permutation of," "any one or more of," etc. Claims or descriptions that include "or" between one or more members of a group are considered satisfied if one, more than one, or all of the group members are present in, employed in, or otherwise relevant to a given product or process unless indicated to the contrary or otherwise evident from the context.

Where ranges are given herein, the endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

While this invention has been particularly shown and described with references to example embodiments thereof, it will be understood by those skilled in the art that the various changes in form and details may be made therein without departing from the scope of the invention encompassed by the appended claims.

Further advantages of the present immunological compositions and adjuvants of the present invention can be achieved by those skilled in the art based upon the embodiments described herein and are thus specifically within the scope of the present invention.

Throughout this specification and claims which follow, unless the context requires otherwise, the word "comprise", and variations such as "comprises" or "comprising", will be understood to imply the inclusion of a stated integer or group of integers or steps but not the exclusion of any other integer or group of integers.

Persons skilled in the art will appreciate that numerous variations and modifications will become apparent. All such variations and modifications which become apparent to persons skilled in the art, should be considered to fall within the spirit and scope that the invention broadly appearing before described.

EXAMPLES

Example 1

Improved Performance Utilizing a Membrane

Figure 16A:
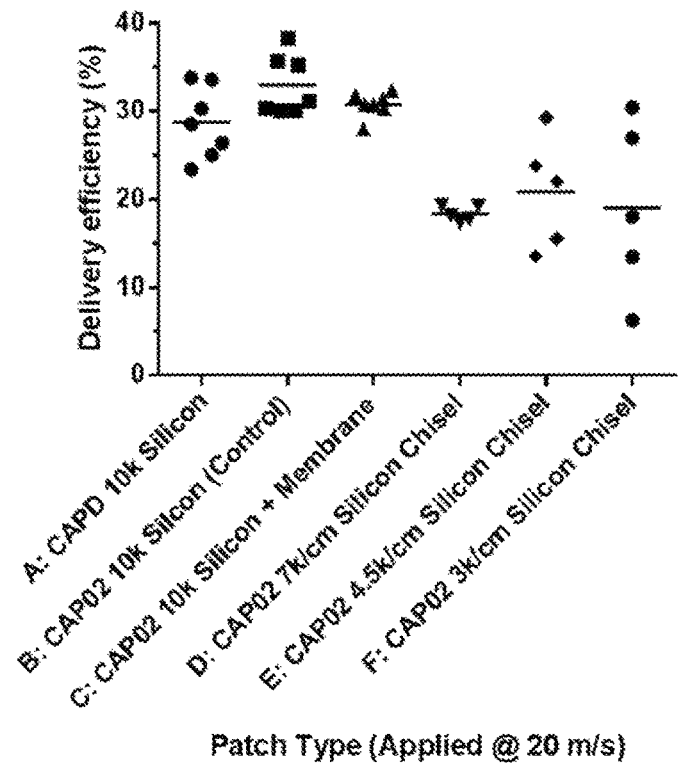
FIG. 16A is a graph of the delivery efficiency of several different microprojection arrays applied to pig skin and FIG. 16B is a graph of the penetration depth of several different microprojection arrays applied to pig skin.
Figure 16B:
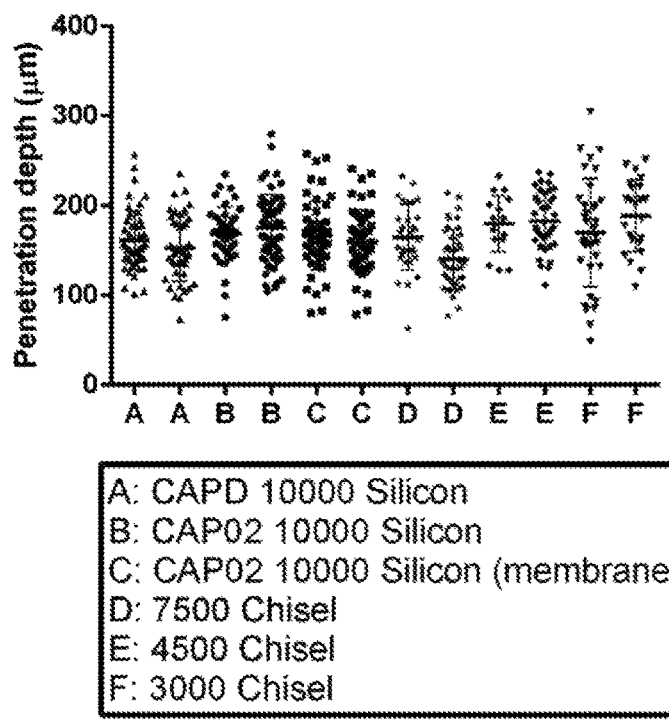

In order to investigate the effects of a linear low-density polyethylene (LLPDE) membrane on the delivery efficiency and variability of penetration of microprojection arrays carrying C14-labelled HPV type 11 antigen in two groups of pig skin derived from the rump of a pig. Silicon microprojection arrays of 10×10 mm having 10000 microprojections were coated at an antigen loading of 50 μg designed to deliver 12.5 μg of antigen to the skin at a 25% transfer efficiency. In one group a 10 μm LLPDE membrane was fixed between the microprojection array and the pig skin. In a second group no membrane was used. Animal's identification number was recorded and the first animal was anesthetized in accordance with normal procedures and record that the animal is unconscious. Animals' sex and weight were recorded and the suitable skin site areas were identified by assessing the skin surface and rejecting areas where visible signs of injury have occurred, e.g. scabs, visible skin wounds/scratches, etc. Any site contamination was removed by gently washing the area with water, dry and record. Clipper and/or shavers were used to remove hair and stubble from the skin surface. The applicator identification was recorded and the timer was set for a 2 min count-down. The applicator was used to apply the patch and the timer started. The patch was delivered at 20 m/s. The patch remained on the application site for the 2 minutes and was removed. The site was checked for any patch debris or bleeding and record. An erythema assessment and edema assessment was performed. The membrane also appeared to decrease erythema caused by patch application. The results are shown in FIGS. 16A and B. The use of the membrane improves the deviation in the distribution of the delivery efficiency of the microprojections meaning the distribution of the delivery efficiency is tighter with the membrane than without. Without the membrane the value was 33.0±3.4% (CV: 10.3%) whereas with the membrane the value was 30.7±1.4% (CV: 4.6%).

The invention claimed is:

1. A device for applying a microprojection array to a skin surface comprising:
   a) a housing having an upper and lower portion and having an internal face and an external face wherein the external face has a flexible section that when collapsed actuates the device;
   b) a cantilevered ring;
   wherein the microprojection array has a mass of from about 0.1 grams to about 0.5 grams and is directly contacted by the cantilevered ring when the cantilevered ring is activated and wherein the microprojection array achieves a velocity of greater than 20 meters/second and wherein the microprojection array is releasably detached from the device after the microprojection array is contacted by the cantilevered ring; and
   c) a skin contact applicator base that attaches to the housing.

2. The device of claim 1 wherein the flexible section of the housing is in the upper portion of the housing.

3. The device of claim 1 wherein the device is a disposable device.

4. The device of claim 1 wherein a desiccant is included in the housing and/or molded parts of the device.

5. The device of claim 1 wherein the microprojection array has a mass from about 0.3 grams.

6. The device of claim 1 wherein the internal portion of the device is sterile.

7. The device of claim 1 wherein the housing forms a sealed sterile barrier and once used the device can be disassembled without contaminated features contacting the user.

8. The device of claim 1 wherein the cantilevered ring is comprised of stainless steel.

9. The device of claim 1 wherein the cantilevered ring is from about 0.5 to about 1.5 mm in height.

10. The device of claim 1 wherein the cantilevered ring is symmetrical.

11. The device of claim 1 wherein the device is a single use device.

12. The device of claim 1 wherein a dessicant is included inside the device.

13. The device of claim 1 wherein the density of microprojections on the microprojection array is between 2500 to 7500/cm$^2$.

14. The device of claim 1, wherein the cantilevered ring is not directly attached to the microprojections of the microprojection array.

15. The device of claim 1 wherein the velocity of the microprojection array is at least 25 meters/second.

16. The device of claim 1 wherein the velocity of the microprojection array is at least 30 meters/second.

17. The device of claim 1, wherein a spigot is connected to the back of the microprojection array.

18. The device of claim 1 further comprising a cover to at least partially cover the skin contact applicator base.

19. The device of claim 18 wherein the cover keeps the device sterile and prevents fluids from getting in the device.

20. The device of claim 18 wherein the cover is a foil seal.

21. A device for applying a microprojection array to a skin surface comprising:
   a) a housing having a flexible section and a base defining an opening that in use is provided in contact with the skin surface; and
   b) a biasing member supported by the housing and movable from a first position to a second position upon deformation of the flexible section, wherein the biasing member urges the microprojection array which has a mass of from about 0.1 grams to about 0.5 grams into engagement with a skin surface through the opening such that the microprojection array achieves a velocity of from about 20 to about 26 meters/second and wherein the microprojection array is releasably detached from the device after contact with the biasing member.

22. The device of claim 21 wherein the biasing member is a cantilevered ring.

23. A device for applying a microprojection array to a skin surface comprising:
   a) a housing having an upper and lower portion and having an internal face and an external face wherein the external face has a flexible section that when collapsed actuates the device;
   b) a cantilevered ring;
   wherein the microprojection array has a mass of from about 0.1 grams to about 0.5 grams and is directly contacted by the cantilevered ring when the cantilevered ring is activated and which achieves a velocity of from 20 to 50 meters/second and wherein the microprojection array is releasably detached from the device after contact with the cantilevered ring and wherein the only contact between the cantilevered ring and the microprojection array to expel the microprojection array is when the ring impacts the microprojection array sending the microprojection toward the skin; and
   c) a skin contact applicator base that attaches to the housing.

* * * * *

UNITED STATES PATENT AND TRADEMARK OFFICE
CERTIFICATE OF CORRECTION

| | |
|---|---|
| PATENT NO. | : 11,147,954 B2 |
| APPLICATION NO. | : 15/548065 |
| DATED | : October 19, 2021 |
| INVENTOR(S) | : Michael Carl Junger et al. |

It is certified that error appears in the above-identified patent and that said Letters Patent is hereby corrected as shown below:

On the Title Page

<u>Column 2, Item (57) ABSTRACT:</u>
"wherein the external face a flexible"
Should read:
-- wherein the external face has a flexible --

Signed and Sealed this
Fourteenth Day of February, 2023

Katherine Kelly Vidal
*Director of the United States Patent and Trademark Office*